(12) United States Patent
Lauber et al.

(10) Patent No.: US 11,414,785 B2
(45) Date of Patent: Aug. 16, 2022

(54) AFFINITY RESINS AND SAMPLE PREPARATION DEVICES BASED ON CARTILAGINOUS FISH IGNAR DERIVED BINDING DOMAINS

(71) Applicant: Waters Technologies Corporation, Milford, MA (US)

(72) Inventors: Matthew A. Lauber, North Smithfield, RI (US); Xiaoxiao Liu, Natick, MA (US); Beatrice Muriithi, Attleboro, MA (US); Edouard S. P. Bouvier, Stow, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 16/990,568

(22) Filed: Aug. 11, 2020

(65) Prior Publication Data

US 2021/0047637 A1 Feb. 18, 2021

Related U.S. Application Data

(60) Provisional application No. 62/885,917, filed on Aug. 13, 2019.

(51) Int. Cl.
*C40B 40/10* (2006.01)
*C12N 15/10* (2006.01)

(52) U.S. Cl.
CPC .......... *C40B 40/10* (2013.01); *C12N 15/1093* (2013.01); *C07K 2317/569* (2013.01)

(58) Field of Classification Search
None
See application file for complete search history.

(56) References Cited

U.S. PATENT DOCUMENTS

2010/0092470 A1\* 4/2010 Bhatt ................. C07K 16/00
424/133.1
2012/0070436 A1\* 3/2012 Easeman ............. A61P 37/02
424/134.1

FOREIGN PATENT DOCUMENTS

WO 2002048193 A2 6/2002
WO 2005007677 A2 1/2005
(Continued)

OTHER PUBLICATIONS

Backmann et al. "A label-free immunosensor array using single-chain antibody fragments." PNAS. 102.41(2005): 14587-14592.
(Continued)

*Primary Examiner* — Christian C Boesen
(74) *Attorney, Agent, or Firm* — Womble Bond Dickinson (US) LLP; Deborah M. Vernon

(57) ABSTRACT

The present disclosure relates to protein arrays and methods of using the same for the detection, quantification and characterization of biomolecules that specifically bind to the array among various other biomolecules in a biological sample. Specifically, the present disclosure relates to protein arrays that include a plurality of immunoglobulin molecules derived from shark single-domain heavy chain antibody lacking light-chains but including at least one variable antigen-binding domain with a binding site for an antigen. The immunoglobulin molecules are immobilized on a substrate via a linker. Further encompassed herein are diagnostic devices and kits, comprising the protein array and methods of using same.

18 Claims, 11 Drawing Sheets

Specification includes a Sequence Listing.

(56) References Cited

FOREIGN PATENT DOCUMENTS

| WO | 2010033913 | A1 | 3/2010 |
| WO | 2010136480 | A1 | 12/2010 |
| WO | 2019063726 | A1 | 4/2019 |

OTHER PUBLICATIONS

International Search Report and Written Opinion issued in International Application No. PCT/IB2020/057553 dated Nov. 16, 2020.
Leow et al. "Single Domain Antibodies as New Biomarker Detectors." Diagnostics. 7(2017): 1-33.
Liu et al. "Oriented immobilization of proteins on solid supports for use in biosensors and biochips: a review." Microhim. Acta. 183(2016): 1-19.
Saerens et al. "Engineering Camel Single-Domain Antibodies and Immobilization Chemistry for Human Prostate-Specific Antigen Sensing." Anal. Chem. 77(2005): 7547-7555.

* cited by examiner

|  | PDB code | FW1 22-24 residues | CDR1 6-10 residues | FW2 10-12 residues | |
|---|---|---|---|---|---|
| anti-Albumin | 4HGK | MGWSCIILFLVATATGAHSTRVDQTPRTATRETGESLTINCVLTDTSYPLYSTYWYRKNP | | | 60 |
| anti-Gingipain K | 2COQ | ------------------------ARVDQTPRIATKETGESLTINCVLRDTACALDSTNWYRTKL | | | 41 |
| anti-Lysozyme | 1SQ2 | ------------------------ARVDQTPRSVTKETGESLTINCVLRDASYALGSTCWYRKKS | | | 41 |
| anti-Lysozyme | 2I25 | ------------------------ARVDQTPQRITKETGESLTINCVVRDSRCVLSTGYWYRKPP | | | 41 |
|  |  | :******  :*;******    *; :*;****;; *: |  |  |  |

|  | HV2 4-8 residues | FW3 9-11 residues | HV4 4-8 residues | FW4 20-22 residues | CDR3 7-21 residues | |
|---|---|---|---|---|---|---|
| 4HGK | GSSNKEQISISGRYVESVNKGTKSFSLRIKDLTVADSATVICRAM------------GTNIW | | | | | 110 |
| 2COQ | GSTKEQTISIGGRYSETVDEGSNSASLTIRDLRVEDSGTYKCCKAYRRCA---F--NTGVG | | | | | 96 |
| 1SQ2 | GEGNEESISKGGRYVETVNSGSKSFSLRINDLTVEDGGTYRCGLGVAGGYCDYALCSSRY | | | | | 101 |
| 2I25 | GSRNEESISDGGRYVETVNRGSKSFSLRINDLTVKDSGTYRCKPESRYGSYD-AVCAALN | | | | | 100 |
|  | *  ;::  :** .:***  *;**  ;****.  * ..,.,:* * |  |  |  |  |  |

|  | FW5 8-10 residues | |
|---|---|---|
| 4HGK | TGDGAGTVLTVNHHHHHH--- | 128 |
| 2COQ | YKEGAGTVLTVK-------- | 108 |
| 1SQ2 | AECGDGTAVTVN-------- | 113 |
| 2I25 | DQYGGGTVVTVNAAAHHHHHH | 121 |
|  | *  .,;; |  |

FIG. 3

SEQUENCE LISTING

```
<160> NUMBER OF SEQ ID NOS: 9

<210> SEQ ID NO 1
<211> LENGTH: 113
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (24)..(35)
<223> OTHER INFORMATION: Xaa can be any naturally occurring amino acid
<220> FEATURE:
<221> NAME/KEY: misc_feature
<222> LOCATION: (39)..(41)
<223> OTHER INFORMATION: Xaa can be any naturally occurring amino acid
<220> FEATURE:
<221> NAME/KEY: misc_feature
<222> LOCATION: (43)..(48)
```

```
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid

<400> SEQUENCE: 1

Xaa Arg Val Asp Gln Thr Pro Xaa Xaa Xaa Thr Xaa Glu Thr Gly Glu
1               5                   10                  15

Ser Leu Thr Ile Asn Cys Val Xaa Xaa Xaa Xaa Xaa Xaa Xaa Xaa Xaa
            20                  25                  30

Xaa Xaa Xaa Trp Tyr Arg Xaa Xaa Xaa Gly Xaa Xaa Xaa Xaa Xaa Xaa
        35                  40                  45

Ile Ser Xaa Xaa Gly Arg Tyr Xaa Glu Xaa Xaa Xaa Xaa Xaa Xaa Xaa
    50                  55                  60

Ser Xaa Ser Leu Xaa Ile Xaa Asp Leu Xaa Val Xaa Asp Xaa Xaa Thr
65                  70                  75                  80

Tyr Xaa Cys Xaa Xaa Xaa Xaa Xaa Xaa Xaa Xaa Xaa Xaa Xaa Xaa Xaa
                85                  90                  95
```

Xaa Xaa Xaa Xaa Xaa Xaa Xaa Xaa Gly Xaa Gly Thr Xaa Xaa Thr Val
                100                 105                 110

Xaa

<210> SEQ ID NO 2
<211> LENGTH: 103
<212> TYPE: PRT
<213> ORGANISM: Artificial Sequence
<220> FEATURE:
<223> OTHER INFORMATION: Sythetic polypeptide

<400> SEQUENCE: 2

Thr Arg Val Asp Gln Thr Pro Arg Thr Ala Thr Arg Glu Thr Gly Glu
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ile Trp Thr Gly Asp Gly Ala
                85                  90                  95

Gly Thr Val Leu Thr Val Asn
            100

<210> SEQ ID NO 3
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 3

Ala Arg Val Asp Gln Thr Pro Arg Ile Ala Thr Lys Glu Thr Gly Glu
1               5                   10                  15

Ser Leu Thr Ile Asn Cys Val Leu Arg Asp Thr Ala Cys Ala Leu Asp
                20                  25                  30

Ser Thr Asn Trp Tyr Arg Thr Lys Leu Gly Ser Thr Lys Glu Gln Thr
            35                  40                  45

Ile Ser Ile Gly Gly Arg Tyr Ser Glu Thr Val Asp Glu Gly Ser Asn
        50                  55                  60

Ser Ala Ser Leu Thr Ile Arg Asp Leu Arg Val Glu Asp Ser Gly Thr
65                  70                  75                  80

Tyr Lys Cys Lys Ala Tyr Arg Cys Ala Phe Asn Thr Gly Val Val Gly
                85                  90                  95

Tyr Lys Glu Gly Ala Gly Thr Val Leu Thr Val Lys
            100                 105

<210> SEQ ID NO 4
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 4

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Glu Gly Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Leu Gly Val Ala Gly Gly Tyr Cys Asp Tyr Ala Leu
                85                  90                  95

Cys Ser Ser Arg Tyr Ala Glu Cys Gly Asp Gly Thr Ala Val Thr Val
                100                 105                 110

Asn
```

<210> SEQ ID NO 5
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 5

```
Ala Arg Val Asp Gln Thr Pro Gln Arg Ile Thr Lys Glu Thr Gly Glu
1               5                   10                  15

Ser Leu Thr Ile Asn Cys Val Val Arg Asp Ser Arg Cys Val Leu Ser
            20                  25                  30

Thr Gly Tyr Trp Tyr Arg Lys Pro Pro Gly Ser Arg Asn Glu Glu Ser
        35                  40                  45

Ile Ser Asp Gly Gly Arg Tyr Val Glu Thr Val Asn Arg Gly Ser Lys
    50                  55                  60

Ser Phe Ser Leu Arg Ile Asn Asp Leu Thr Val Lys Asp Ser Gly Thr
65                  70                  75                  80

Tyr Arg Cys Lys Pro Glu Ser Arg Tyr Gly Ser Tyr Asp Ala Val Cys
                85                  90                  95

Ala Ala Leu Asn Asp Gln Tyr Gly Gly Gly Thr Val Val Thr Val Asn
                100                 105                 110
```

<210> SEQ ID NO 6
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 6

```
His His His His His His
1               5
```

<210> SEQ ID NO 7
<211> LENGTH: 27
<212> TYPE: PRT
<213> ORGANISM: Artificial Sequence
<220> FEATURE:
<223> OTHER INFORMATION: Synthetic polypeptide

```
<400> SEQUENCE: 7

Phe Asn Trp Tyr Val Asp Gly Val Glu Val His Asn Ala Lys Thr Lys
1               5                   10                  15

Pro Arg Glu Glu Gln Tyr Asn Ser Thr Tyr Arg
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 8

Phe Asn Trp Tyr Val Asn Gly Ala Glu Val His His Ala Gln Thr Lys
1               5                   10                  15

Pro Arg Glu Thr Gln Tyr Asn Ser Thr Tyr Arg
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 9

Phe Ser Trp Phe Val Asp Asp Val Glu Val His Thr Ala Gln Thr Arg
1               5                   10                  15

Pro Pro Glu Glu Gln Phe Asn Ser Thr Phe Arg
            20                  25
```

AFFINITY RESINS AND SAMPLE PREPARATION DEVICES BASED ON CARTILAGINOUS FISH IGNAR DERIVED BINDING DOMAINS

RELATED APPLICATIONS

This application claims the benefit of U.S. Provisional Application No. 62/885,917, filed on Aug. 13, 2019. The entire teachings of the above applications are incorporated herein by reference.

SEQUENCE LISTING

This application incorporates by reference the Sequence Listing contained in the ASCII text file with the file name W102994_10720.txt, created Jul. 27, 2020 with the size of 12 KB, being submitted concurrently herewith.

FIELD OF THE TECHNOLOGY

The technology relates to modified cartilaginous fish-derived immunoglobulin-like molecules, IgNARs, having desirable functions, such as binding affinity to one or more targets. In particular, the technology relates to modified shark IgNAR derived variable-domain peptides immobilized on a substrate via a linker, their use in capturing target substances and to a method and/or a test kit for detecting and enriching target substances.

BACKGROUND

Affinity capture is one approach that can be used to address a multitude of challenges related to the analysis of biological samples through enriching analytes, enhancing selectivity and improving limits of detection. Affinity capture is typically a starting point to the analysis of biologics produced by cell culture and the analysis of biotherapeutics circulating in patient or animal biofluids. In biopharmaceutical drug development, affinity capture remains critical to the determination and monitoring of dosing, pharmacokinetics and pharmacodynamics. In particular, affinity capture can be used in the quantitation of a biopharmaceutical as it is sampled from animals during pre-clinical trials and from patients during clinical work. Ideally, the sample preparation steps need to be simple and robust yet for them to also be sensitive enough to confer a wide dynamic range of measurement. Similar attributes are preferred in the sample preparation approaches for biomarker quantitation assays intended for disease diagnostics or for applications in personalized medicine. Currently, a multitude of detection methods can be employed, ranging from sandwich assays like enzyme linked immunosorbents assays (ELISA) to selective detection by mass spectrometry. However, the existing assays have various shortcomings including their over reliance on immunoglobulins as a ligand modality. The use of intact immunoglobulins as capture ligands pose significant steric hindrance due to their large size, which can ultimately affect various critical parameters of an affinity capture assay including the binding capacity of immunoglobulin based affinity resins, slower than desired kinetics and sub-optimal on-off rates due to increased conformational heterogeneity.

SUMMARY

Oligonucleotide-based aptamers and small affimer peptides have been proposed as alternatives to immunoglobulins as ligands in affinity capture due to their small, sizes, but they have failed to achieve wide spread adoption. Single domain antibodies derived from homodimeric immunoglobulins have been used as ligands in affinity capture assays. These proteinaceous molecules are less than 20 kDa in size and can be used to afford inordinately high coverages and correspondingly high binding capacity affinity resins. Camelid antibodies, homodimeric with a single variable domain called a VHH, have garnered the most attention, as they can be easily prepared and isolated for affinity capture. A VHH single domain antibody is constructed from three complementarity determining regions spaced apart from one another by four canonical framework sequences. Camelid derived nanobodies have proven to be highly stable, as exemplified by the fact that binding activity can sometimes be maintained up to temperatures in excess of 70° C. They can also be immobilized with comparatively high surface coverages and it would be possible to engineer them to have binding interactions that are free of any major steric hindrance owing to their small size.

Despite the availability of these VHH based materials, there is a need to devise affinity resins with ligands of a different format to facilitate the development of assays and tools effective for a wide diversity of analytes, particularly to access novel human antigens that do not bind to the existing VHH based affinity resins. The shark immunoglobulin super-family protein, the immunoglobulin New Antigen Receptor (igNAR), was originally isolated and identified from the nurse shark, Ginglymostoma cirratum, in 1995 (Greenberg et al., (1995), Nature, 374, 168-173). Single domain antibody derived from igNARs are homodimeric like the camelid antibodies and contains a variable domain (a vNAR domain) with about 100 residues similar to the VHH domain. However, unlike a VHH domain, a vNAR domain has only two complementarity determining regions (CDRs). Its otherwise third CDR region is effectively split by a conserved region into two hypervariable loops. Because igNARs are derived by convergent evolution having a phylogeny far separated from mammals, they can be a means to access more novel and potentially stronger binding domains against human antigens, especially if compared to an immunoglobulin based single domain antibody derived from a mammalian species, such as a camelid species. The use of igNARs as a substrate capture ligand in an affinity assay or sample preparation is desirable based on its evolutionary conservation, stability, structural diversity and strong antigenicity effects.

The present technology provides affinity resins, affinity sample preparation devices, diagnostic devices based on modified igNAR protein sequences that have useful properties, such as enhanced selectivity to analytes that improve limits of analyte detection in various biological samples. More specifically, the technology relates to affinity resins, affinity sample preparation devices and diagnostic devices based on shark igNAR derived binding domains having a template vNAR sequence described below.

SEQ ID NO. 1
N-terminus-XRVDQTPXXXTXETGESLTINCV[cdr1]XXX

XWYRXXXG[hv2]ISXXGRYXEX[hv4]SXSLX

IXDLXVXDXXTYXCXX[cdr3]GXGTXXTVX C-terminus where one letter abbreviations are used for amino acid residues, X denotes any proteogenic amino acid residue, and [cdr1] corresponds to a 6 to 10 amino acid complementarity determining region, [cdr3] to a 7 to 21 residue complementarity determining region, [hv2] to a 4 to 8 residue hypervariable loop, and [hv4] to a 4 to 8 amino acid hypervariable loop. In some embodiments, the igNAR derived binding domains, having a template vNAR sequence described above, are immobilized to substrates suitable for performing affinity capture and sample enrichment. The technology further relates to modified igNAR protein scaffolds that can be used for the selection of de novo binding domains having desired binding characteristics, such as affinity for new target molecules and/or high affinity for known or new ligands. In addition, the technology also relates to methods for the detection of proteins from a biological sample, methods of comparing protein expression patterns and purification using the affinity resins and affinity sample preparation devices described herein. The affinity resins, affinity sample preparation devices, diagnostic devices based on modified igNAR protein sequences described herein can have advantageous properties including, but not limited to, binding novel antigens having unique specificities and/or bind to antigens with higher binding affinity than existing resins. The present technology facilitates high capacity, robust solid phases, surfaces, and devices for use in a multitude of off-line and online sample preparations, ranging from the quantitation of monoclonal antibodies in biofluids to extraction and quantitation of biomarkers.

In one aspect, provided herein is a protein array comprising a plurality of immunoglobulin molecules derived from shark single-domain heavy chain antibody lacking lightchains. The plurality of immunoglobulin molecules has at least one variable antigen-binding domain with at least one binding site for an antigen. In one embodiment, the plurality of immunoglobulin molecules is immobilized on a substrate via a linker. The protein array can include one or more of the following embodiments.

In some embodiments, the plurality of immunoglobulin molecules of the protein array includes a single type of immunoglobulin molecule that binds to same epitopes in the antigen. The plurality of immunoglobulin molecules of the protein array can include at least two types of immunoglobulin molecules that bind to different epitopes in a single antigen. In some embodiments, the plurality of immunoglobulin molecules of the protein array includes at least two types of immunoglobulin molecules that bind to different epitopes in two different antigens. The plurality of immunoglobulin molecules can include at least two complementarity determining regions (CDRs). In some embodiments, the plurality of immunoglobulin molecules also includes at least two hypervariable loops that have a function that is equivalent to the function of a third CDR region. The plurality of immunoglobulin molecules can include the variable antigen-binding domain with an amino acid sequence of SEQ ID NO: 1. In some embodiments, the plurality of immunoglobulin molecules includes the variable antigen-binding domain with an amino acid sequence selected from the group consisting of SEQ ID NO: 2, SEQ ID NO: 3, SEQ ID NO: 4 and SEQ ID NO: 5.

In some embodiments, one or more amino acid residues in a framework region of the plurality of immunoglobulin molecules is substituted by a different amino acid to facilitate immobilization on the substrate. A C-terminal residue of the plurality of immunoglobulin molecules can be substituted with a cysteine residue. In some embodiments, a C-terminal residue of the plurality of immunoglobulin molecules is substituted with a non-natural amino acid residue. The non-natural amino acid residue can be selected from a group consisting of p-acetylphenylalanine, p-azidomethyl-L-phenylalanine and N6-((2-azidoethoxy)carbonyl)-L-lysine. In some embodiments, one or more amino acid residues are appended to a C-terminus of the plurality of immunoglobulin molecules. A poly Histidine tag can be appended to the plurality of immunoglobulin molecules. In some embodiments, a peptide with SEQ ID NO. 6 is appended to the plurality of immunoglobulin molecules. A cysteine residue can be appended to the plurality of immunoglobulin molecules. In some embodiments, a non-natural amino acid residue is appended to the immunoglobulin molecule. The non-natural amino acid residue can be selected from a group consisting of p-acetylphenylalanine, p-azidomethyl-L-phenylalanine and N6-((2-azidoethoxy)carbonyl)-L-lysine.

In some embodiments, the plurality of immunoglobulin molecules is immobilized on the substrate by the linker through a covalent linkage. The covalent linkage can be achieved by one or more processes selected from group consisting of a reductive amination, a NHS activated electrophilic substitution, a carbodiimide dehydration and a Michael addition reaction. In some embodiments, the plurality of immunoglobulin molecules is attached to the substrate by a cleavable linker. In some embodiments, the plurality of immunoglobulin molecules is attached to the substrate by a non-cleavable linker.

In some embodiments, the substrate is a porous or non-porous solid phase made from a material comprising polystyrene, polypropylene, polyvinylchloride, polyacrylamide, celluloses, dextrans, synthetic polymers, co-polymers, latex, silica, organosilica, agarose, metal, glass, or carbon, or a combination thereof. In some embodiments, the substrate comprises all or part of a surface of a microvolume plate, a pipet tip, a channel, a tube, a microtitre plate, a vial, a column, a silica bead, a polymeric bead, or a monolith. The substrate can be a porous or non-porous solid phase comprising a magnetic material. In some embodiments, the substrate is coated with a magnetic layer. The substrate can be a porous or non-porous solid phase comprising a non-magnetic material. In some embodiments, the substrate is coated with a non-magnetic layer. The substrate can include a silica or organosilica surface having a Maleimide polyethylene glycol (PEG) silane bonded to the silica or organosilica surface, wherein the PEG repeat can range from 3 to 300.

In some embodiments, the antigen is selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, insulin, modified insulin drugs, ghrelin, drugs of abuse and their metabolites, hemoglobin, albumins, glucagon, viral vectors and their capsid proteins, adenoassociated virus, lentivirus, gamma retrovirus, adenovirus, hepatitis c, hepatitis b, hepatitis a, HIV, biomarkers for cardiovascular disease (Trends Cardiovasc Med. 2017 Feb.; 27(2)), human growth hormone, erythropoietin, cancer immunotherapy biomarkers (Computational and Structural Biotechnology Journal Volume 17, 2019, Pages 484-497), host cell proteins from murine and chinese ovary hamster cells, amyloid beta, tau, phospho-tau, muromonab, edrecolomab, capromab, ibritumomab tiuxetan, blinatumomab, abciximab, rituximab, basiliximab, infliximab, cetuximab, brentuximab vedotin, siltuximab, palivizumab, trastuzumab, alemtuzumab, omalizumab, bevacizumab, natalizumab, ranibizumab, eculizumab, certolizumab, tocilizumab, pertuzumab, obinutuzumab, trastuzumab emtansine, pembrolizumab, vedolizumab, elotuzumab, idarucizumab, mepolizumab, adalimumab, pegfilgrastim, panitumumab, romiplostim, canakinumab, golimumab, ofatumumab, ustekinumab, denosumab, belimumab, ipilimumab, raxibacumab, efmoroctocog alfa, eftrenonacog alfa, nivolumab, ramucirumab, alirocumab, asfotase alfa, daratumumab, evolocumab, necitumumab, secukinumab, abatacept, rilonacept, aflibercept, and belatacept.

In another aspect, the technology relates to a diagnostic device. The device includes the protein array with a plurality of immunoglobulin molecules derived from shark single-domain heavy chain antibody lacking light-chains and having at least one variable antigen-binding domain. The plurality of immunoglobulin molecules in the protein array of the diagnostic device has at least one binding site for an antigen, and the plurality of immunoglobulin molecules are immobilized on a substrate via a linker. The diagnostic device can include one or more the embodiments described herein.

In yet a further aspect, the technology relates to a method of determining the presence of one or more proteins of interest in a sample. The method includes contacting a sample of one or more proteins with the protein array under conditions suitable for binding of the one or more proteins of interest to the plurality of immunoglobulin molecules of the protein array. The protein array can be any of the protein arrays described herein, including any of the embodiments described herein. The method also includes capturing the one or more proteins with the protein array, wherein the at least one variable antigen-binding domain of the plurality of immunoglobulin molecules of the protein array binds specifically to the one or more proteins of interest. The method also includes washing the captured one or more proteins of interest with a solvent. The presence of the one or more proteins of interest is detected. The method can include one or more of the embodiments described herein.

In some embodiments, the at least one variable antigen-binding domain of the plurality of immunoglobulin molecules of the protein array binds specifically to the one or more proteins with a dissociation constant (KD) of $1\times10^{-6}$ M or less. The detection of the one or more proteins can include measuring a functionality of the one or more proteins. In one embodiment, the detection of the one or more proteins includes performing an enzyme linked immunosorbent assay (ELISA). The detection of the one or more proteins can also include using a detector to detect the presence of the one or more proteins. In some embodiments, the detector is a mass spectrometer.

The one or more proteins can be selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, insulin, modified insulin drugs, ghrelin, drugs of abuse and their metabolites, hemoglobin, albumins, glucagon, viral vectors and their capsid proteins, adenoassociated virus, lentivirus, gamma retrovirus, adenovirus, hepatitis c, hepatitis b, hepatitis a, HIV, biomarkers for cardiovascular disease (Trends Cardiovasc Med. 2017 Feb.; 27(2)), human growth hormone, erythropoietin, cancer immunotherapy biomarkers (Computational and Structural Biotechnology Journal Volume 17, 2019, Pages 484-497), host cell proteins from murine and chinese ovary hamster cells, amyloid beta, tau, phospho-tau, muromonab, edrecolomab, capromab, ibritumomab tiuxetan, blinatumomab, abciximab, rituximab, basiliximab, infliximab, cetuximab, brentuximab vedotin, siltuximab, palivizumab, trastuzumab, alemtuzumab, omalizumab, bevacizumab, natalizumab, ranibizumab, eculizumab, certolizumab, tocilizumab, pertuzumab, obinutuzumab, trastuzumab emtansine, pembrolizumab, vedolizumab, elotuzumab, idarucizumab, mepolizumab, adalimumab, pegfilgrastim, panitumumab, romiplostim, canakinumab, golimumab, ofatumumab, ustekinumab, denosumab, belimumab, ipilimumab, raxibacumab, efmoroctocog alfa, eftrenonacog alfa, nivolumab, ramucirumab, alirocumab, asfotase alfa, daratumumab, evolocumab, necitumumab, secukinumab, abatacept, rilonacept, aflibercept, and belatacept.

In one aspect, provided herein is a method of comparing protein expression patterns of two samples. The method includes contacting a first sample of one or more proteins with any of the protein arrays described herein, including any of the embodiments described herein, under conditions suitable for binding of the one or more proteins of the first sample to the plurality of immunoglobulin molecules of the protein array. The method also includes contacting a second sample of one or more proteins with the protein array under conditions suitable for binding of the one or more proteins of the second sample to the plurality of immunoglobulin molecules of the protein array. The method also includes detecting the amount of protein bound to each of the protein arrays described in the contacting steps described above. The amounts of protein bound to the protein array contacted with the first sample is compared to the corresponding amounts of protein bound to the protein array contacted with the second sample. The method can include one or more of the embodiments described herein.

In some embodiments, the detection of the one or more proteins in the first and second sample includes measuring a functionality of the one or more proteins. In some embodiments, the detection of the one or more proteins in the first and the second sample, is achieved by performing an ELISA. A detector can be used to detect the amount of protein bound to each of the protein arrays. In some embodiments, the detector is a mass spectrometer.

The first sample and the second sample can be two mammalian cells or a population of two mammalian cells. In some embodiments, the one or more proteins of interest of the first and second sample are selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, insulin, modified insulin drugs, ghrelin, drugs of abuse and their metabolites, hemoglobin, albumins, glucagon, viral vectors and their capsid proteins, adenoassociated virus, lentivirus, gamma retrovirus, adenovirus, hepatitis c, hepatitis b, hepatitis a, HIV, biomarkers for cardiovascular disease (Trends Cardiovasc Med. 2017 Feb.; 27(2)), human growth hormone, erythropoietin, cancer immunotherapy biomarkers (Computational and Structural Biotechnology Journal Volume 17, 2019, Pages 484-497), host cell proteins from murine and chinese ovary hamster cells, amyloid beta, tau, phospho-tau, muromonab, edrecolomab, capromab, ibritumomab tiuxetan, blinatumomab, abciximab, rituximab, basiliximab, infliximab, cetuximab, brentuximab vedotin, siltuximab, palivizumab, trastuzumab, alemtuzumab, omalizumab, bevacizumab, natalizumab, ranibizumab, eculizumab, certolizumab, tocilizumab, pertuzumab, obinutuzumab, trastuzumab emtansine, pembrolizumab, vedolizumab, elotuzumab, idarucizumab, mepolizumab, adalimumab, pegfilgrastim, panitumumab, romiplostim, canakinumab, golimumab, ofatumumab, ustekinumab, denosumab, belimumab, ipilimumab, raxibacumab, efmoroctocog alfa, eftrenonacog alfa, nivolumab, ramucirumab, alirocumab, asfotase alfa, daratumumab, evolocumab, necitumumab, secukinumab, abatacept, rilonacept, aflibercept, and belatacept.

In another aspect, provided herein is a method for enrichment or purification of one or more proteins of interest in a sample. The method includes contacting a sample of one or more proteins with any of the protein arrays described herein, including any of the embodiments described herein, under conditions suitable for binding of the one or more proteins of the sample to the plurality of immunoglobulin molecules of the protein array. The method also includes capturing the one or more proteins of interest with the protein array such that at least one variable antigen-binding domain of the plurality immunoglobulin molecules of the protein array binds specifically to the one or more proteins of the sample. The method also includes eluting the one or more proteins of the sample from the protein array. The method also includes determining the purity of the one or more proteins of the sample. The method can include one or more of the embodiments described herein.

In some embodiments, the determination of the purity of the sample includes measuring the functionalities of one or more proteins of the sample. The one or more proteins of the sample can be selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, insulin, modified insulin drugs, ghrelin, drugs of abuse and their metabolites, hemoglobin, albumins, glucagon, viral vectors and their capsid proteins, adenoassociated virus, lentivirus, gamma retrovirus, adenovirus, hepatitis c, hepatitis b, hepatitis a, HIV, biomarkers for cardiovascular disease (Trends Cardiovasc Med. 2017 Feb.; 27(2)), human growth hormone, erythropoietin, cancer immunotherapy biomarkers (Computational and Structural Biotechnology Journal Volume 17, 2019, Pages 484-497), host cell proteins from murine and chinese ovary hamster cells, amyloid beta, tau, phospho-tau, muromonab, edrecolomab, capromab, ibritumomab tiuxetan, blinatumomab, abciximab, rituximab, basiliximab, infliximab, cetuximab, brentuximab vedotin, siltuximab, palivizumab, trastuzumab, alemtuzumab, omalizumab, bevacizumab, natalizumab, ranibizumab, eculizumab, certolizumab, tocilizumab, pertuzumab, obinutuzumab, trastuzumab emtansine, pembrolizumab, vedolizumab, elotuzumab, idarucizumab, mepolizumab, adalimumab, pegfilgrastim, panitumumab, romiplostim, canakinumab, golimumab, ofatumumab, ustekinumab, denosumab, belimumab, ipilimumab, raxibacumab, efmoroctocog alfa, eftrenonacog alfa, nivolumab, ramucirumab, alirocumab, asfotase alfa, daratumumab, evolocumab, necitumumab, secukinumab, abatacept, rilonacept, aflibercept, and belatacept.

In one aspect, provided herein is a method of evaluating a disease condition in a tissue in an organism. The method includes contacting a diseased tissue in an organism comprising one or more proteins of interest with the protein array (i.e., any of the protein arrays described herein, including any of the embodiments described herein) under conditions suitable for binding of the one or more proteins of interest to the plurality of immunoglobulin molecules of the protein array. The method also includes capturing the one or more proteins of interest with the protein array such that at least one variable antigen-binding domain of the plurality immunoglobulin molecules of the protein array binds specifically to the one or more proteins of the sample. The method also includes detecting the presence of the one or more proteins of interest and comparing the expression of the one or more proteins of interest in the diseased tissue with a corresponding amount of protein in a healthy tissue. An altered expression of the one or more proteins of interest in the diseased tissue is indicative of the disease condition. The method can include one or more of the embodiments described herein.

In some embodiments, the detection of the one or more proteins includes measuring a functionality of the one or more proteins. The detection of the one or more proteins can include performing an enzyme linked immunosorbent assay (ELISA). In some embodiments, the detection of the one or more proteins also includes using a detector to detect the presence of the one or more proteins. The detector can be a mass spectrometer. In some embodiments, the one or more proteins are selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, insulin, modified insulin drugs, ghrelin, drugs of abuse and their metabolites, hemoglobin, albumins, glucagon, viral vectors and their capsid proteins, adenoassociated virus, lentivirus, gamma retrovirus, adenovirus, hepatitis c, hepatitis b, hepatitis a, HIV, biomarkers for cardiovascular disease (Trends Cardiovasc Med. 2017 Feb.; 27(2)), human growth hormone, erythropoietin, cancer immunotherapy biomarkers (Computational and Structural Biotechnology Journal Volume 17, 2019, Pages 484-497), host cell proteins from murine and chinese ovary hamster cells, amyloid beta, tau, phospho-tau, muromonab, edrecolomab, capromab, ibritumomab tiuxetan, blinatumomab, abciximab, rituximab, basiliximab, infliximab, cetuximab, brentuximab vedotin, siltuximab, palivizumab, trastuzumab, alemtuzumab, omalizumab, bevacizumab, natalizumab, ranibizumab, eculizumab, certolizumab, tocilizumab, pertuzumab, obinutuzumab, trastuzumab emtansine, pembrolizumab, vedolizumab, elotuzumab, idarucizumab, mepolizumab, adalimumab, pegfilgrastim, panitumumab, romiplostim, canakinumab, golimumab, ofatumumab, ustekinumab, denosumab, belimumab, ipilimumab, raxibacumab, efmoroctocog alfa, eftrenonacog alfa, nivolumab, ramucirumab, alirocumab, asfotase alfa, daratumumab, evolocumab, necitumumab, secukinumab, abatacept, rilonacept, aflibercept, and belatacept.

In some embodiments, the disease condition is selected from a group consisting of a cancer, a type I diabetes, a type II diabetes, an immunomodulatory disease, an autoimmune disease, an inflammatory disease, an endocrinal disease, a pulmonary disease, a hepatic disease, a cardiovascular disease, and a neurodegenerative disease.

In another aspect, the technology features a kit for determining the presence of one or more proteins of interest in a sample. The kit includes the protein array (i.e., any of the protein arrays described herein, including any of the embodiments described herein). The kit also includes instructions for use of the protein array in a method for detecting one or more proteins of interest in a sample. The kit can include one or more of the embodiments described herein.

In another aspect, the technology features a method of detecting of one or more proteins of interest in a sample. The method includes contacting the sample comprising the one or more proteins of interest with any one of the protein arrays described herein under conditions suitable for binding of the one or more proteins of interest to the plurality of immunoglobulin molecules of the protein array. The one or more proteins of interest are captured with the protein array wherein the at least one variable antigen-binding domain of the plurality immunoglobulin molecules of the protein array binds specifically to the one or more proteins of interest. The method also includes eluting the one or more proteins of interest from the protein array and detecting the one or more proteins of interest with a detector. The method can include one or more of the embodiments described herein.

In some embodiments, the detector is a mass spectrometer. The method can also include separating the eluted one or more proteins of interest with liquid chromatography prior to detecting the one or more proteins of interest. The liquid chromatography can be reversed-phase liquid chromatography.

BRIEF DESCRIPTION OF THE DRAWINGS

The technology will be more fully understood from the following detailed description taken in conjunction with the accompanying drawings, in which:

FIG. 3 provides information about an immunoglobulin molecule that can include a variable antigen-binding domain having the amino acid sequence that is at least 80%, at least 85%, at least 90%, at least 95%, at least 98%, or at least 100%, identical to any one of the four sequences, 4HGK (SEQ ID NO.2), 2COQ (SEQ ID NO.3), 1SQ2 (SEQ ID NO.4) and 2I25 (SEQ ID NO.5), according to an illustrative embodiment of the technology.

FIG. 4A shows the HPLC profile of Biotin-FR-27 and FIG. 4B shows the MS profile of Biotin-FR-27.

FIG. 5A shows the HPLC profile of KLH-CR-28 and FIG. 5B shows the MS profile of KLH-CR-28.

FIG. 6A shows the HPLC profile of the Control peptide #1 and FIG. 6B shows the MS profile of Control peptide #1.

FIG. 7A shows the HPLC profile of the Control peptide #2 and FIG. 7B shows the MS profile of Control peptide #2.

DETAILED DESCRIPTION

Definitions

Figure 1:
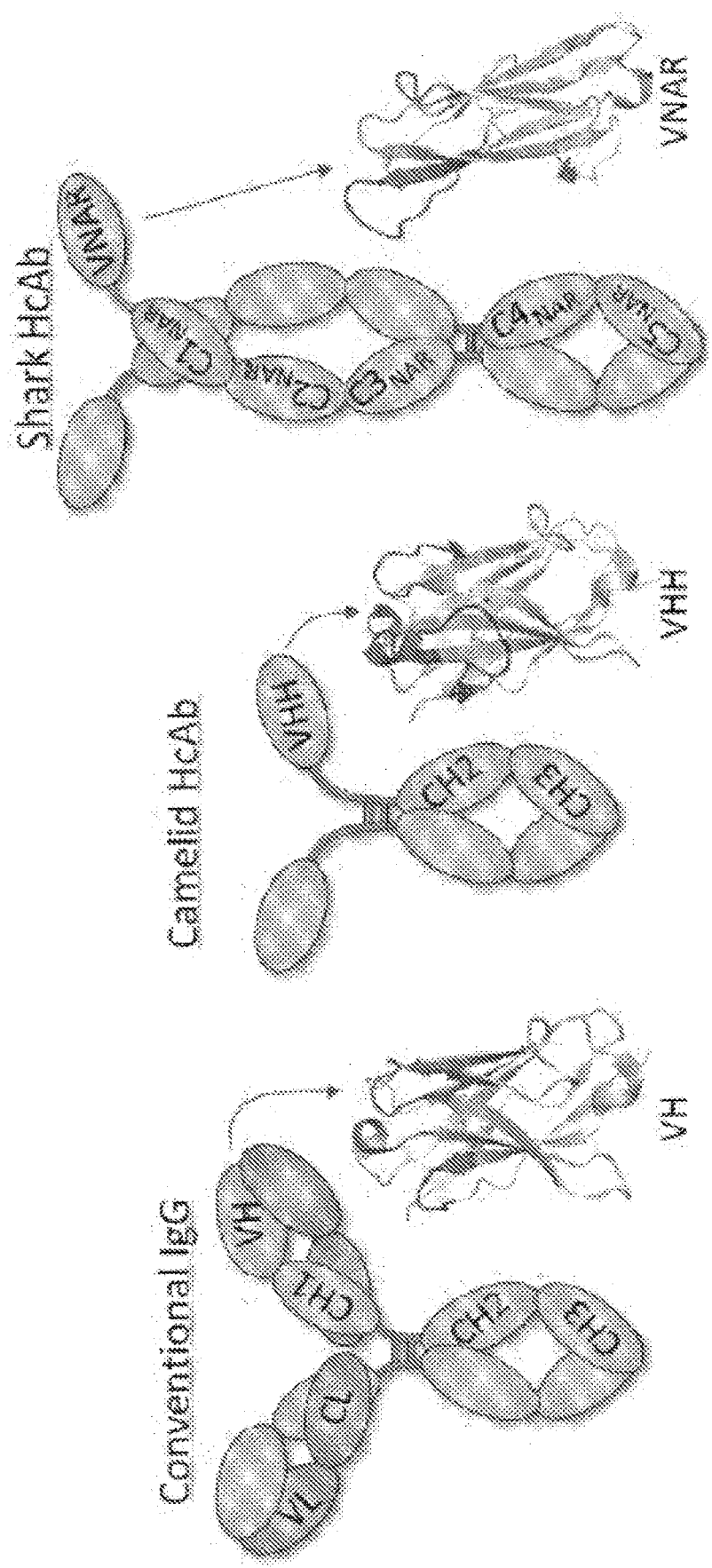
FIG. 1 is a schematic illustration of a representative shark immunoglobulin super-family protein, the immunoglobulin New Antigen Receptor (igNAR), according to an illustrative embodiment of the technology. The illustration provides a comparison of an igNAR with a schematic of conventional IgG1 and a schematic of a single domain antibody. Also shown are the cartoon representations of the corresponding VNAR, Vh and VHH domains.

In order that the technology may be more readily understood, certain terms are first defined. In addition, it should be noted that whenever a value or range of values of a parameter are recited, it is intended that values and ranges intermediate to the recited values are also part of this disclosure. It is also to be noted that as used herein and in the appended claims, the singular forms "a," "and" and "the" include plural references unless the context clearly dictates otherwise.

The term "altered expression," as used herein, refers to "changed," "modified," and in certain embodiments, "silenced" (e.g., gene silencing) expression of a gene or its protein product. The term "expression" in the term "altered expression" refers to either or both transcription and translation. Where only transcription is intended, the phrase "gene expression" may be used. Where only translation of a protein is intended, the phrase "protein expression" may be used.

The term "antigen" as used herein, refers to any desirable biomolecule or ligand that may be recognized (i.e. bound) by the igNAR molecules of the disclosure, such as nucleic acids (e.g. DNA or RNA), small organic or inorganic molecules, proteins or peptides. A suitable antigen is a protein, and a particularly suitable antigen is a peptide sequence or "epitope" of a protein.

The term "array" in the term "protein array", refers to an arrangement of entities (e.g., ligands, capture-agents, biomolecules such as proteins, immunoglobulin molecules) in a pattern on a substrate. The terms "array", "micro-array", and "chip" are used herein interchangeably. They refer to an arrangement, on a substrate surface, of hybridizable array elements, preferably, a plurality of immunoglobulin molecules derived from igNARs of known sequences. Each immunoglobulin molecule is immobilized to a discrete spot (i.e., a defined location or assigned position) on the substrate surface. Although the pattern is typically a two-dimensional pattern, the pattern can also be a three-dimensional pattern. The term "protein" in the term "protein array", refers to an array made up of a polymer of amino acid residues linked together by peptide bonds. The term, as used herein, refers to an array made up of proteins, polypeptides, and peptides of any size, structure, or function. Typically, however, a protein array will consist of proteins/peptides that are at least 10 amino acid residues long. A protein array can be made up of proteins that can be naturally occurring, recombinant, or synthetic, or any combination of these. A protein array can also be made up of fragments of a naturally occurring proteins or peptides. A protein in the protein array can be a single molecule or may be a multi-molecular complex. The term protein array also includes arrays made up of amino acid polymers in which one or more amino acid residues is an artificial chemical analogue of a corresponding naturally occurring amino acid. An amino acid polymer in which one or more amino acid residues is an "unnatural" amino acid, not corresponding to any naturally occurring amino acid, is also encompassed by the use of the term "protein" herein.

The terms "bound," "captured," and "hybridized," are used interchangeably, referring to the binding of the protein of interest to the binding domain of the immunoglobulin molecule derived from igNARs via cognate recognition (e.g., covalent, hydrophobic, vanderwaals or hydrophilic interactions). The terms "specific binding," "binding specificity," refer to a process in which a protein of interest preferentially binds the immunoglobulin molecule derived from igNARs, under stringent conditions (e.g., in the presence of competitor proteins with a lower degree of binding to the same epitopes and/or different epitopes in the immunoglobulin molecule). In preferred embodiments of the present disclosure, these terms more specifically refer to a process in which a protein of interest (or multiple proteins)

from a test sample preferentially binds to an immunoglobulin molecule and to a lesser extent or not at all, to other immunoglobulin molecules, for example, when these immunoglobulin molecules are immobilized on a substrate to form a protein array.

The term "derived from" is meant to refer to the resulting protein molecule with one or more mutations/substitutions/deletions in comparison to the primary amino acid sequence of the protein on which the resulting protein molecule is based upon. Thus an immunoglobulin molecule derived from shark igNAR is meant to indicate that the immunoglobulin molecule has at least one or more mutations/substitutions/deletions in comparison to the primary amino acid sequence of the shark iGNAR, such as theWobbegong igNAR. The term "derived from" can also refer to the resulting protein molecule that has been selected the from the shark iGNAR, such as theWobbegong igNAR, with a desired activity (e.g. binding affinity for a selected target ligand). In some other instance, the term "derived from" can also refer to the resulting protein molecule that has a a desired activity (e.g. binding affinity for a selected target ligand) but that further includes one or more mutations/substitutions/deletions to the primary amino acid sequence of a in comparison to the primary amino acid sequence of the protein on which the resulting protein molecule is based upon. Thus, the modified igNAR peptide of the disclosure may have one or more (e.g. 1, 2, 3, 4, 5 or more) chemically modified amino acid side chains compared to the parent igNAR from which it is derived. Suitable modifications may include pegylation, sialylation and glycosylation. In addition, or alternatively, a modified igNAR peptide may contain one or more (e.g. 1, 2, 3, 4, 5 or more) amino acid mutations, substitutions or deletions to the primary sequence of a parent igNAR peptide An "immunoglobulin molecule", as used here refers to an antibody or an antibody fragment which may be derived from natural sources or partially/wholly synthetically produced. Typically, each immunoglobulin molecule maintains a specific binding ability to one antigens of interest. However, immunoglobulin molecule with binding specificity to a) more than one epitope of a single antigen and/or b) two or more antigens, is comprehended by the term in the present disclosure. The term also covers any protein having a binding domain which is homologous or largely homologous to an immunoglobulin binding domain. The immunoglobulin molecule can be a member of any immunoglobulin class, including any of the human classes: IgG, IgM, IgA, IgD, and IgE. Derivatives of the IgG class, however, are preferred in the present disclosure. The immunoglobulin molecules can be derived from any organism (e.g., cartilaginous fish like shark, human) or can be recombinantly produced. The term "antibody fragment" refers to any derivative of an antibody which is less than full-length. Preferably, the antibody fragment retains at least a significant portion of the full-length antibody that is a determinant of its specific binding ability. Examples of antibody fragments include, but are not limited to, sdAb, Fab, Fab', F(ab')2, scFv, Fv, dsFv diabody, and Fd fragments. The antibody fragment can be produced by any means. For instance, the antibody fragment may be enzymatically or chemically produced by fragmentation of an intact antibody or it can be recombinantly produced from a gene encoding the partial antibody sequence. Alternatively, the antibody fragment can be wholly or partially synthetically produced. The antibody fragment can optionally be a domain antibody fragment. With either a variable light chain or a variable heavy chain. Alternatively, the fragment can comprise multiple chains which are linked together, for instance, by disulfide linkages. The fragment can also optionally be a multimolecular complex. A functional antibody fragment will typically comprise at least about 10-50 amino acids and more typically will comprise at least about 100 amino acids. In preferred embodiments of the present disclosure, immunoglobulin molecule specifically refers to the binding domain of an immunoglobulin molecule derived from shark igNAR that has at least one or more mutations/substitutions/deletions in comparison to the primary amino acid sequence of the shark iGNAR, such as theWobbegong igNAR, and, lacks light-chains but comprises at least one variable antigen-binding domain (e.g., vNAR with an amino acid sequence selected from the group consisting of SEQ ID NO: 2, SEQ ID NO: 3, SEQ ID NO: 4 and SEQ ID NO: 5).

The term "hypervariable loop" refers to the surfaces/regions in the immunoglobulin molecule that confers antigen recognition and specific binding to the antigen. Generally, the hypervariable loops differ in sequence and in length between different immunoglobulin molecules, and which are connected to a conserved framework structure. Both heavy and light chain variable regions of an immunoglobulin molecule, each contain three hypervariable loop domains also referred to as Complementarity Determining Regions (CDRs). The three CDRs are designated as CDR1-CDR3 and are encoded by the recombined variable region gene segments.

A "linker" is a spacer molecule that covalently links the substrate to the immunoglobulin molecule. The term "cleavable linker", as used herein, is defined as a spacer molecule characterized by having a bond that can be cleaved under certain conditions. The cleavage could be a chemically-induced (e.g., change in pH) cleavage or a photo-induced cleavage. The cleavable linker, typically has one functional group that binds to a substrate, or to a moiety on the substrate and a second functional group that can be conjugated to an amino acid on the immunoglobulin molecule. The cleavable linkers of the disclosure can have a third functional group, a nucleophilic group, that can attack the ester bond and cleave it thereby. The linker provides for cleavage of the immunoglobulin molecule after the capture of the analyte/antigen is complete. The term "non-cleavable linker", as used herein, is defined as a spacer molecule characterized by having a bond that cannot be cleaved under any conditions The "immunoglobulin New Antigen Receptor (igNAR)," described in the present disclosure belongs to the shark immunoglobulin super-family protein (Greenberg et al., (1995), Nature, 374, 168-173). IgNARs have some structural similarities to mammalian antibody/immunoglobulin proteins and consists of two protein chains each with one variable domain, (generally) five constant domains and long CDR3 loops in the variable domain and, like camelid VHH antibodies.

The term "non-natural amino acid" all amino acid-like compounds that are similar in structure and/or overall shape to one or more of the twenty L-amino acids commonly found in naturally occurring proteins (Ala or A, Cys or C, Asp or D, Glu or E, Phe or F, Gly or G, His or H, He or I1 Lys or K, Leu or L, Met or M, Asn or N, Pro or P, Gln or Q, Arg or R, Ser or S, Thr or T, Val or V1 Trp or W, Tyr or Y, as defined and listed in WIPO Standard ST.25 (1998), Appendix 2, Table 3). "Amino acid analog," "non-canonical amino acid," "unnatural amino acid," "modified amino acid," and the like may all be used interchangeably, and is meant to refer to non-natural amino acids. Non-natural amino acids can also be natural amino acids with modified side chains or backbones. Amino acids can also be naturally occurring amino acids in D-, rather than L-form. Certain analogs with structures or shapes sufficiently close to those of natural amino acids may be erroneously incorporated into proteins by aminoacyl tRNA synthetases (AARSs), especially modified AARSs with relaxed substrate specificity. In some instances, the non-natural amino acids share backbone structures, and/or even the most side chain structures of one or more natural amino acids, with the only difference(s) being containing one or more modified groups in the molecule. Such modification may include, without limitation, substitution of an atom (such as N) for a related atom (such as S), addition of a group (such as methyl, or hydroxyl group, etc.) or an atom (such as Cl or Br, etc.), deletion of a group (supra), substitution of a covalent bond (single bond for double bond, etc.), or combinations thereof. Non-natural amino acids may include α-hydroxy acids, and α-amino acids. The non-natural amino acids can either be naturally occurring or non-natural (e.g., synthesized). As will be appreciated by those in the art, any structure for which a set of rotamers is known or can be generated can be used as a non-natural amino acids. The side chains may be in either the (R) or the (S) configuration (or D- or L-configuration).

As used herein, the term "organism" refers to any organism that has a diseased condition or state. Examples of an organism include, but not limited to, for example, a mammal (e.g., a human, a non-human mammal, a non-human primate, a primate, a laboratory animal, a mouse, a rat, a hamster, a cat, or a dog). In one embodiment, the organism is a human.

The term "sample," "system," and "biological system," are used herein interchangeably and is intended to include a biological fluid, cell, tissue, organ or portion thereof, that includes one or more different molecules such as nucleic acids, polypeptides, or small molecules. In the context of the present disclosure, in vitro, in vivo, and ex vivo systems are considered; and the sample can be a tissue section obtained by biopsy, or cells that are placed in or adapted to tissue culture. A sample can also be a biological fluid specimen such as blood, plasma or serum, cerebrospinal fluid, urine, saliva, seminal plasma, pancreatic juice, and the like. A sample can additionally be a cell extract from any species, including prokaryotic and eukaryotic cells as well as viruses. A tissue or biological fluid specimen can be further fractionated, if desired, to a fraction containing particular cell types. For example, a sample can originate from a living subject (e.g., it may be obtained by drawing blood, or by performing needle biopsy), or from a deceased subject (e.g., it may be obtained at autopsy).

"Single-domain heavy chain antibody", as used herein, refers to a recombinant antibody fragment consisting of either a variable light chain (VL) or the variable heavy chain (VH) domain. Typically, the single-domain heavy chain antibodies have a molecular weight of about 15 kDa.

The term "substrate," or "solid support," refers to the bulk underlying, and core material of the arrays of the disclosure. As used herein, the term "substrate" is not limited to a specific type of support. Rather a large number of supports are available and are known to one of ordinary skill in the art. Substrate includes silica gels, resins, derivatized plastic films, glass beads, cotton, plastic beads, alumina gels, polysaccharides. A suitable substrate may be selected on the basis of desired end use and suitability for various synthetic protocols. The substrate of the present disclosure can be a porous or a non-porous solid made from a material comprising polystyrene, polypropylene, polyvinylchloride, polyacrylamide, celluloses, dextrans, synthetic polymers, co- polymers, latex, silica, organosilica, agarose, metal, glass, or carbon, or a combination thereof. Substrates can also include microvolume plates, pipet tips, channels, tubes, sample vials and labware. A suitable substrate can be irregularly or uniformly shaped particle beads with particle diameters from 0.1 micron to 1000 micron, more preferably 0.5 micron to 200 microns, and pore diameters from 50 Å to 3000 Å, more preferably 90 to 2000 Å

In accordance with the present disclosure there may be employed conventional cell culture methods, chemical synthetic methods and other biological and pharmaceutical techniques within the skill of the art. Such techniques are well-known and are otherwise explained fully in the literature. Standard techniques for growing cells, separating cells, and where relevant, binding and elution of samples from protein arrays and the like, and various separation, enrichment, purification, identification, characterization and quantification of proteins are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Where a range of values is provided, it is understood that each intervening value, to the tenth of the unit of the lower limit unless the context clearly dictates otherwise (such as in the referencing binding affinity ($K_D$) in which case each values falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs.

The vNAR derived affinity ligands of the present disclosure are also predicted to be of value for the purification of biotherapeutics as well as cell and gene therapies, or so-called advanced therapeutic medicinal products. In most situations, these types of drug products are derived from or based on cell culture, fermentation, transient expression, or ex vivo cell manipulations. Because of these complicated processes, there is frequently a requirement to have selective purification procedures that make it possible to control and minimize process-related impurities that can endanger patients by causing adverse, toxicological effects. In the manufacturing of a monoclonal antibody, it has become common practice to use a protein A affinity capture step to concentrate and purify mAbs expressed from mammalian cell cultures. (Ref—https://www.frontiersin.org/articles/10.3389/fbioe.2019.00420/full). Within the burgeoning gene therapy field, it is, meanwhile, coming to be desirable to use affinity chromatography to facilitate the purification of viral vectors.

For in vivo therapies, this affinity capture step can entail the use of a camelid VHH based ligand selective toward various adenoassociated virus serotypes. POROS™ CaptureSelect™ AAV resins from Thermo Fisher Scientific (Waltham, Mass.) are representative of this type of affinity technology. Similar affinity steps might come to also be developed into being critical bioprocessing steps for the preparation of adenoviruses and adenoviral vectored gene therapies.

For ex vivo cell therapies, lentivirus is generally used as a vector, and affinity might come to standardize as an approach to manufacture and purify it as well. During the preparation of an autologous cell therapies, like CAR-T (chimeric antigen receptor T cells), Cell antigens and cell differentiation must be carefully considered. Patient cells are collected by means of apheresis and it is subsequently important to select naïve T-cells for genetic engineering. Affinity can be used in this critically important step to isolate cells based on clusters of differentiation (CD). Naïve T-cells are needed for successful treatment and processing. Phenotype selection is accordingly important. In more than one therapeutic example, CD4+ and CD8+ T cells have been shown to have desirable and amenable to the development of chimeric antigen T cells. CliniMACS® CD4 can be used to enrich CD4+ T cells and is provided by Miltenyi Biotec (Bergisch Gladbach, Germany) in the form of murine anti-CD4 monoclonal antibodies conjugated to superparamagnetic iron dextran particles. This affinity reagent binds CD4, which is an accessory molecule involved in the recognition of foreign antigens in association with MHC class II antigens by T cells. Stem cell selection might also be of importance to some future advance therapies. It is reasonable to suggest that vNAR ligands could be advantageously applied to purify, select, or detect OCT4, a transcription factor involved in the self-renewal of embryonic stem cells, SOX-2, a transcription factor required to maintain pluripotency in undifferentiated embryonic stem cells, or LIN-28, an embryonic stem cell marker. Similarly, vNAR ligands could be applied to deplete human fibroblasts and pluripotent cells from stem cell preparations.

New specificities and alternative ligands options will be needed for each of the above-mentioned bioprocessing examples. The vNAR ligands described herein will help provide promising options for new bioprocessing techniques. Importantly, the ligands of the instant disclosure can be combined with monolithic bioprocessing columns, particles for packed beds, membranes, or fibers. In addition, magnetic beads could be used as an affinity ligand substrate to facilitate separations of intact cells. Companion analytical technologies for these bioprocessing steps might also take advantage of the vNAR ligands. These might include mass cytometry, flow cytometry, fluorescence activated cell sorting, interferometry, or surface plasmon resonance.

Protein Arrays

The present technology is directed to protein arrays with compositions, e.g., affinity resins, and their use in various applications related to separation, detection, extraction, purification, quantification and expression of biomolecules, for example, monoclonal antibodies.

The protein arrays (see, e.g., protein array 200 of FIG. 2) of the present technology include a plurality of immunoglobulin molecules (see, e.g., 205 of FIG. 2) derived from shark single-domain heavy chain antibody (variable domain, a vNAR domain) lacking light-chains but have at least one variable antigen-binding domain with at least one binding site for an antigen. (See, e.g., FIG. 1.) In some embodiments, only one type of immunoglobulin molecules is present on the protein array. In other embodiments, more than one type of immunoglobulin molecules is present on a single protein array, with all of those molecules either binding to the same epitope or different epitopes on the antigen. For example, the protein array can include a variety of monoclonal vNARs to the same epitope on the antigen. In some embodiments, the protein array can include a variety of polyclonal vNARs binding to different epitopes on the same antigen (although, potentially, some of those epitopes can be overlapping). The protein array can include a variety of polyclonal vNARs binding to same epitopes on different antigens. The protein array can include a variety of polyclonal vNARs binding to different epitopes on different antigens (although, potentially, some of those epitopes can be overlapping).

The protein arrays of the technology can have any number of immunoglobulin molecules with different vNARs on a single array. Typically, the protein array with multiple vNARs includes at least about ten different vNARs. The protein array can include at least about 50 different vNARs. In some embodiments, the protein array includes at least about 100 different vNARs. The protein array and include more than about 150 different vNARs or more than about 200 different vNARs. The array can even optionally include more than about 1000 different vNARs. The number of different immunoglobulin molecules on the array can vary depending on the application desired. For example, if the protein array is to be used as a diagnostic tool in quantification of a particular biomarker, a protein array with a single type of immunoglobulin molecule, each with the specificity to the biomarker of interest, can be used. However, for example, if the protein array is to be used for evaluating the status of a diseased tissue (e.g., tumor tissue), a protein array comprising about 50-100 different protein-capture agents can suffice since about 50-100 biomarkers whose expression is known to be indicative of the disease condition, can be captured on the array with vNARs specific for the specific markers. In another example, if the protein array is to be used to measure a multitude of proteins or the total protein content of a cell, then the protein array can include at least about 1000 different vNARs. In yet another example where the array is to be used to compare the protein expression patters of two samples, a limited number of vNARs with specificities to a representative set of proteins can suffice.

In some embodiments, the protein array includes different patches with each of the patches including a different immunoglobulin molecule. For example, a protein array including about 100 patches can include about 100 different immunoglobulin molecules. In another embodiment, each different immunoglobulin molecule can be immobilized on more than one separate patch on the protein array. For example, each different immunoglobulin molecule can optionally be present on 10 different patches. A protein array of the technology, therefore, can include about 1000 patches, but only include less than 1000 patches since each different immunoglobulin molecule is present on multiple different patches to create redundancy, minimize steric effects and increase binding affinity. In some embodiments, the protein array includes a plurality of immunoglobulin molecules that are applied to the surface of a substrate, where the protein array has a surface density of at least 100 sites/cm2, 1000 sites/cm2, 10,000 sites/cm2, 100,000 sites/cm2, or 1,000,000 sites/cm2.

In some embodiments, the immunoglobulin molecule includes a variable antigen-binding domain having the amino acid sequence of SEQ ID NO.1 shown below:

```
                                          SEQ ID NO. 1
XRVDQTPXXXTXETGESLTINCV[cdr1]XXX XWYRXXXG[hv2]ISXXGRYXEX[hv4]SXSLX IXDLXVXDXXTYXCXX[cdr3]GXGTXXTVX
``` where one letter abbreviations are used for amino acid residues, X denotes any proteogenic amino acid residue, and [cdr1] corresponds to a 6 to 10 amino acid complementarity determining region, [cdr3] to a 7 to 21 residue complementarity determining region, [hv2] to a 4 to 8 residue hypervariable loop, and [hv4] to a 4 to 8 amino acid hypervariable loop.

The immunoglobulin molecule can include a variable antigen-binding domain having the amino acid sequence that is at least 80%, at least 85%, at least 90%, at least 95%, at least 98%, or at least 100%, identical to any one of the four sequences, 4HGK (SEQ ID NO.2), 2COQ (SEQ ID NO.3), 1SQ2 (SEQ ID NO.4) and 2125 (SEQ ID NO.5), provided in FIG. 3.

Also included in the technology are variants, analogues, derivatives and fragments having the amino acid sequence of 4HGK (SEQ ID NO.2), 2COQ (SEQ ID NO.3), 1SQ2 (SEQ ID NO.4) and 2125 (SEQ ID NO.5) proteins in which one or more, e.g., 1 to 2, 2 to 3, 3 to 4, 5 to 10, or no amino acid residues are substituted, deleted or added in any combination. These can also include silent substitutions (e.g., substitutions in the framework regions FW1-FW4), additions and deletions, which do not alter the properties and activities of the protein of the present technology. In addition, conservative substitutions where the properties of the immunoglobulin molecule of the present technology are preserved in the variant form compared to the original form can be used. Variants of the technology also include fusion proteins such as the poly histidine tag fused to either the N- and/or the C-termini of any one of 4HGK (SEQ ID NO.2), 2COQ (SEQ ID NO.3), 1SQ2 (SEQ ID NO.4) and 2125 (SEQ ID NO.5). The terms "fragment," "protein fragment," as used herein, refer to a polypeptides comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

In some embodiments, the poly histidine tag is fused to the C-terminus of any one of 4HGK (SEQ ID NO.2), 2COQ (SEQ ID NO.3), 1SQ2 (SEQ ID NO.4), 2125 (SEQ ID NO.5) or variants thereof. The immunoglobulin molecule can include a vNAR domain of any one of 4HGK (SEQ ID NO.2), 2COQ (SEQ ID NO.3), 1SQ2 (SEQ ID NO.4) and 2125 (SEQ ID NO.5) or variants thereof appended to a heterologous peptide sequence. Such heterologous peptide sequence can be a poly-amino acid sequence, for example a plurality of histidine residues or a plurality of lysine residues (suitably 2, 3, 4, 5, or 6 residues), or an immunoglobulin domain (for example an Fc domain). In some embodiments, the heterologous peptide sequence (QAPKVDAKFD, SEQ ID NO. 6) is fused to the C-terminus of any one of 4HGK (SEQ ID NO.2), 2COQ (SEQ ID NO.3), 1SQ2 (SEQ ID NO.4), 2125 (SEQ ID NO.5) or variants thereof. Heterologous peptide sequences can include sequences from other mammalian species, such as murine and human and any heterologous peptides sequences originated from other vNAR domains. In some embodiments, the immunoglobulin molecule includes a vNAR domain of any one of 4HGK (SEQ ID NO.2), 2COQ (SEQ ID NO.3), 1SQ2 (SEQ ID NO.4) and 2125 (SEQ ID NO.5) or variants thereof appended to a single amino acid. The amino acid can be a naturally occurring amino-acid or a non-natural amino acid. In some embodiments, a single cysteine residue is appended to the C-terminus of any one of 4HGK (SEQ ID NO.2), 2COQ (SEQ ID NO.3), 1SQ2 (SEQ ID NO.4), 2125 (SEQ ID NO.5) or variants thereof. In some embodiments, a non-natural amino acid is fused to the C-terminus of any one of 4HGK (SEQ ID NO.2), 2COQ (SEQ ID NO.3), 1SQ2 (SEQ ID NO.4), 2125 (SEQ ID NO.5) or variants thereof. The non-natural amino acid residue can be selected from a group consisting of p-acetylphenylalanine, p-azidomethyl-L-phenylalanine and N6-((2-azidoethoxy)carbonyl)-L-lysine. The fusions to the vNAR domains described herein can provide structural rigidity to the vNAR molecule or provide an additional functional group to either react with a functional group in the linker or react with a moiety in the antigen. In some embodiments, the vNARs of the present technology can be fused to another immunoglobulin variable or constant region, or another vNAR domain. In some embodiments this can be represented as a multimer of monomer vNAR subunits.

Substrates and Linkers

Figure 2:
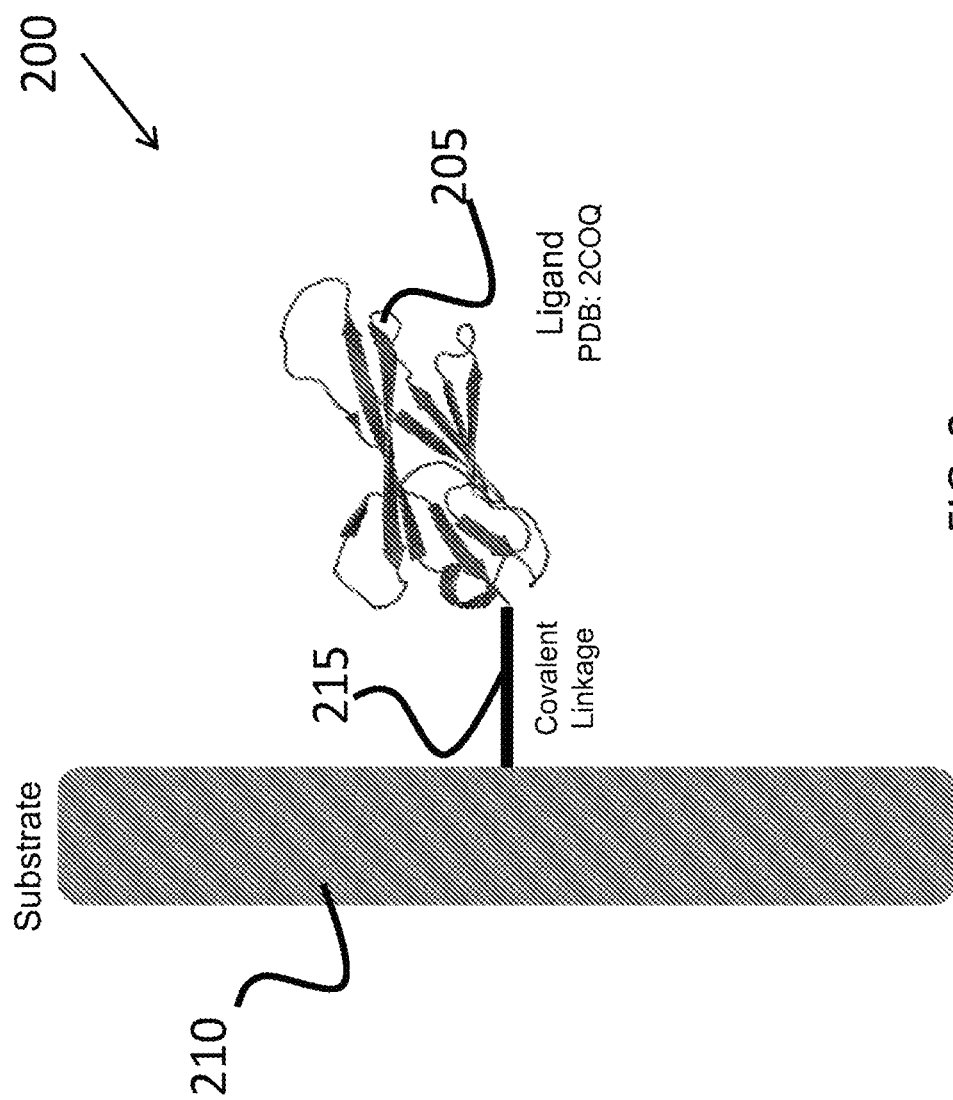
FIG. 2 is a schematic illustration of an igNAR based affinity device, according to an illustrative embodiment of the technology.
Figure 4A:
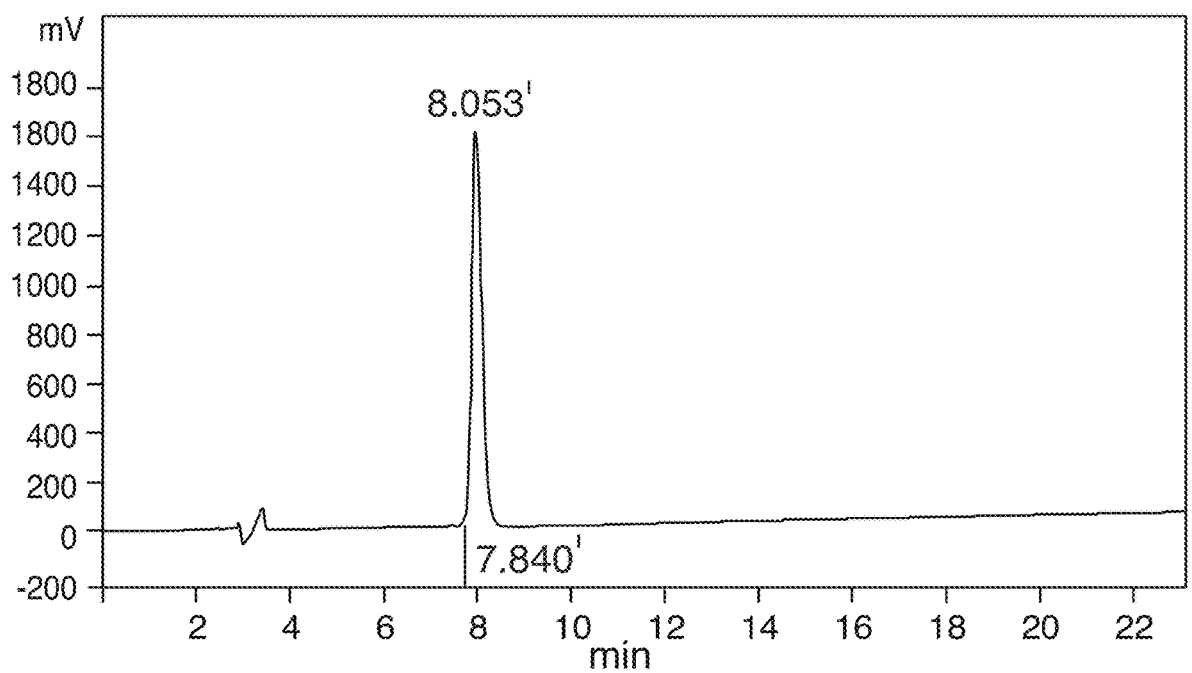
FIG. 4A and FIG. 4B show the HPLC and MS profiles of the peptide Biotin-FR-27.
Figure 4B:
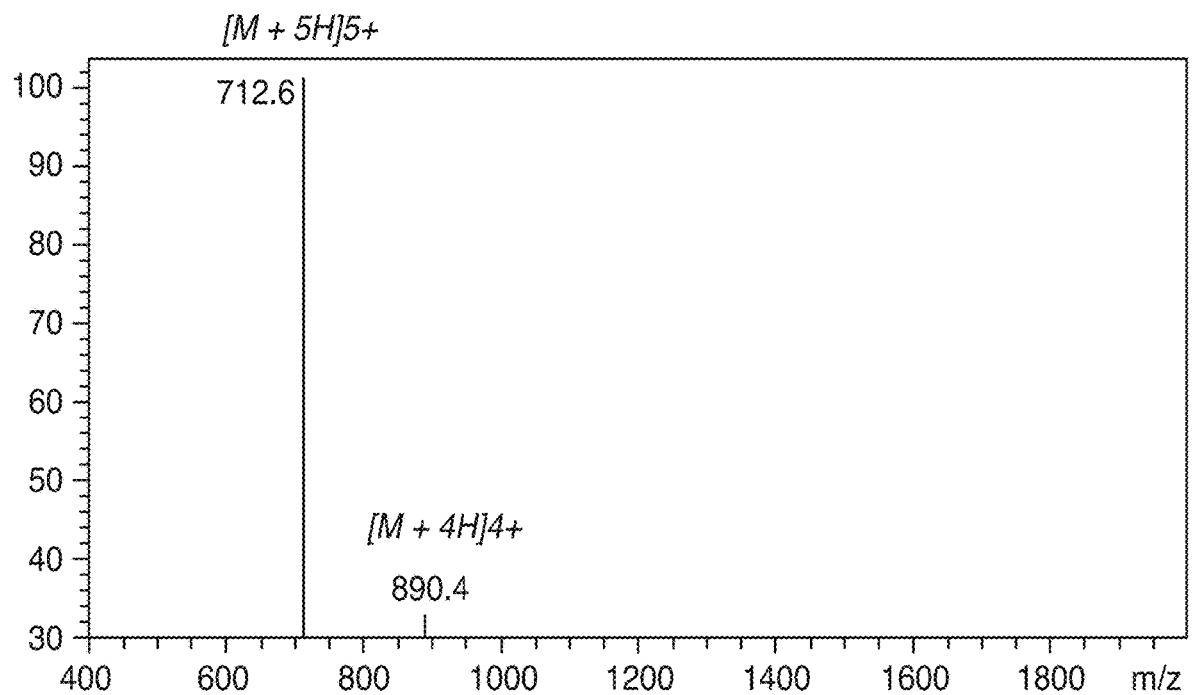
Figure 5A:
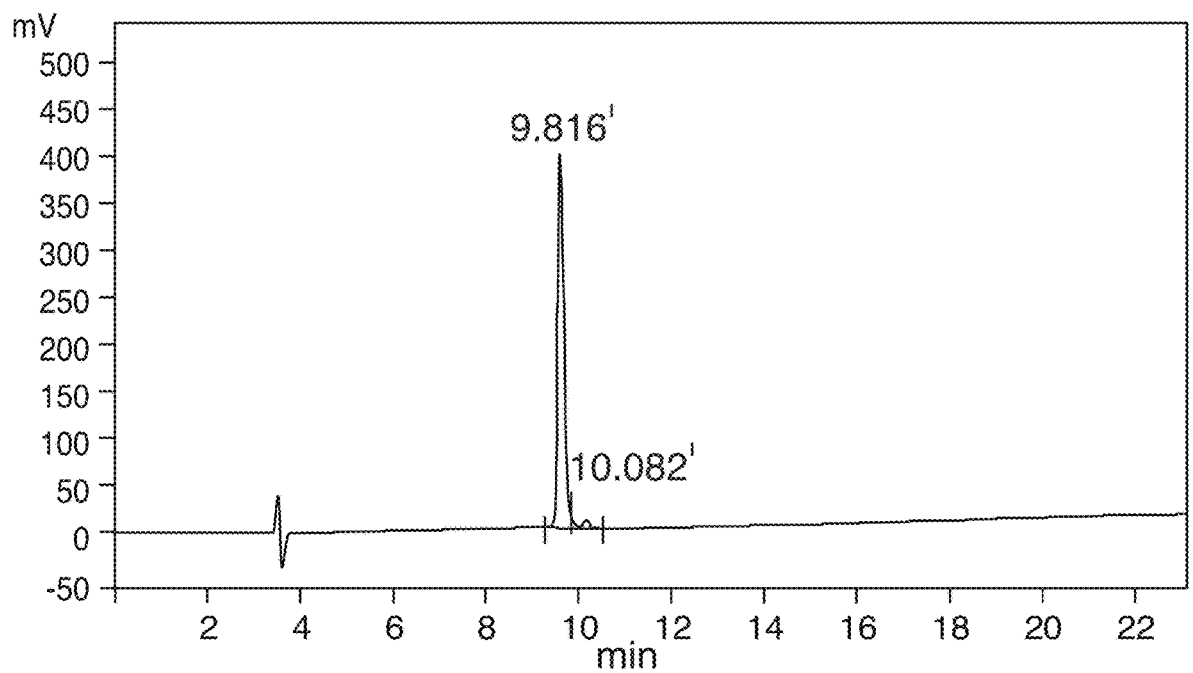
FIG. 5A and FIG. 5B show the HPLC and MS profiles of the peptide KLH-CR-28.
Figure 5B:
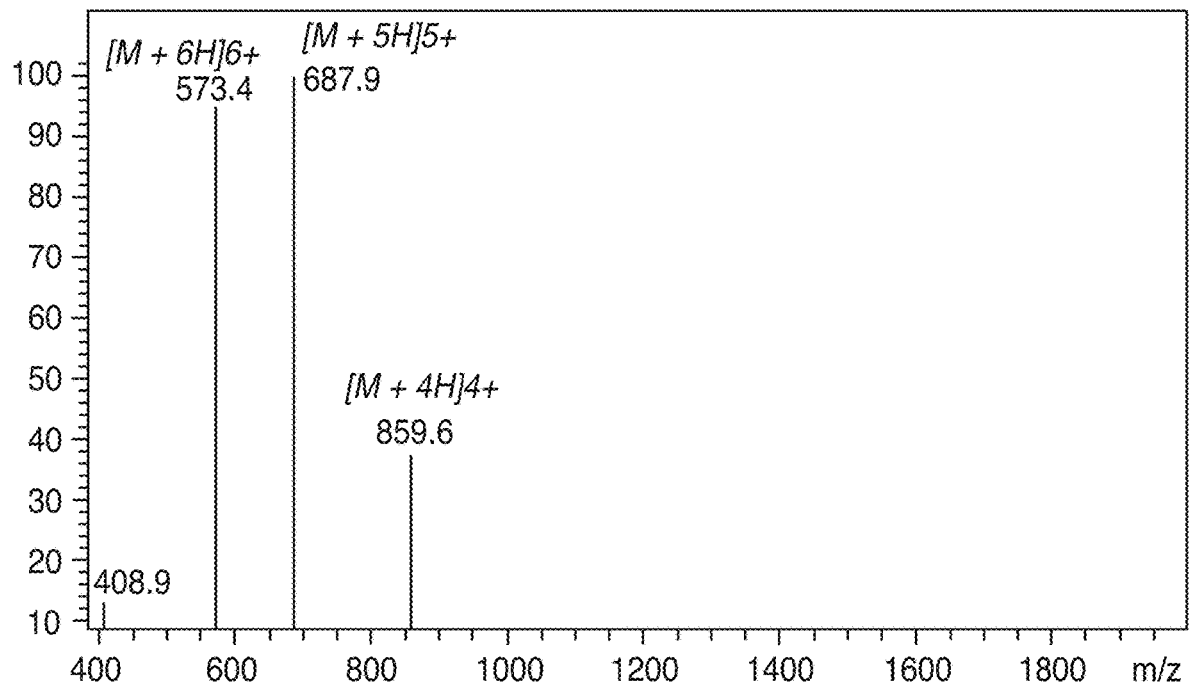
Figure 6A:
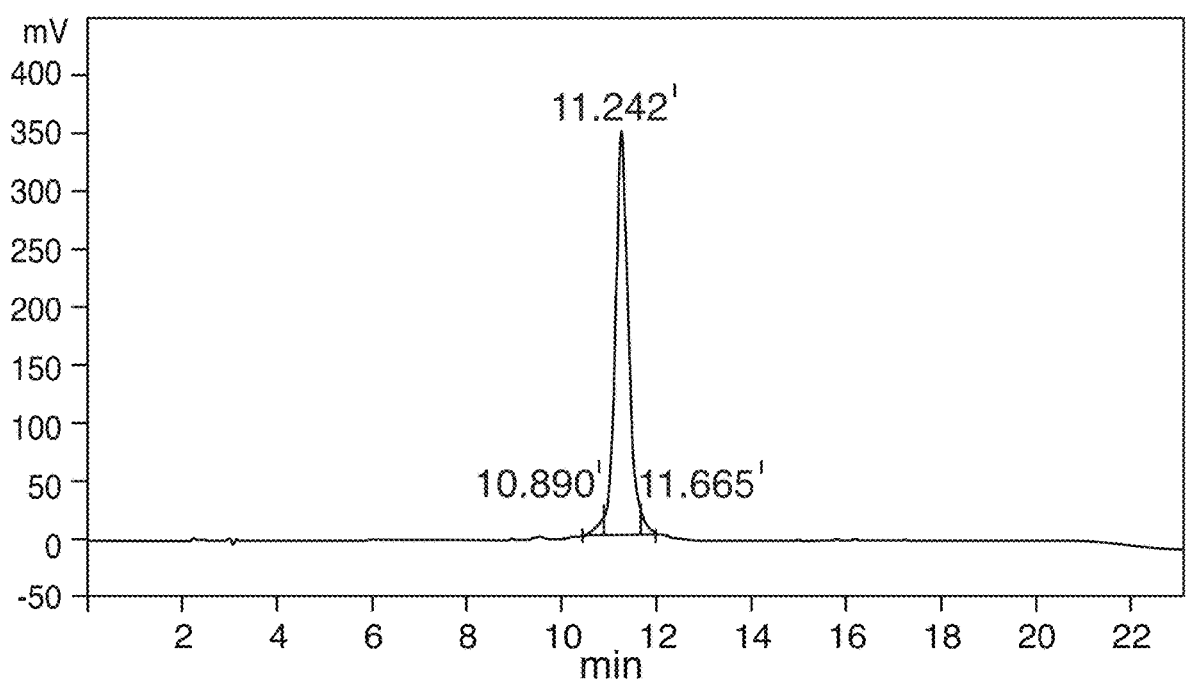
FIG. 6A and FIG. 6B show the HPLC and MS profiles of Control peptide #1.
Figure 6B:
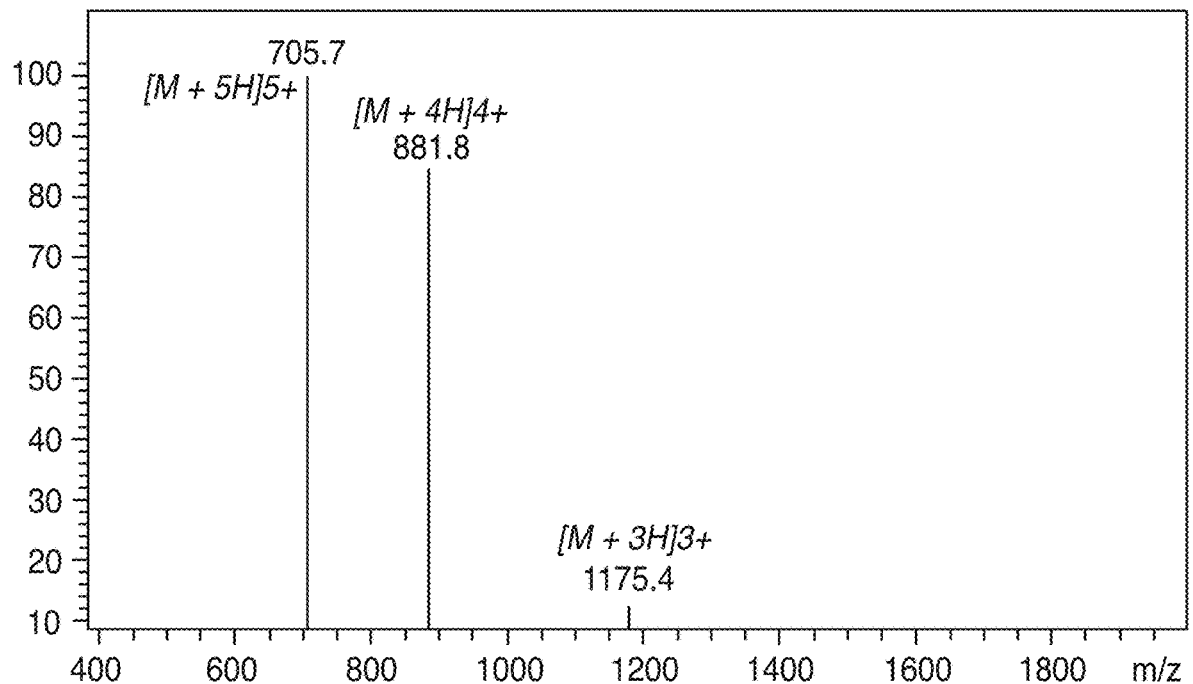
Figure 7A:
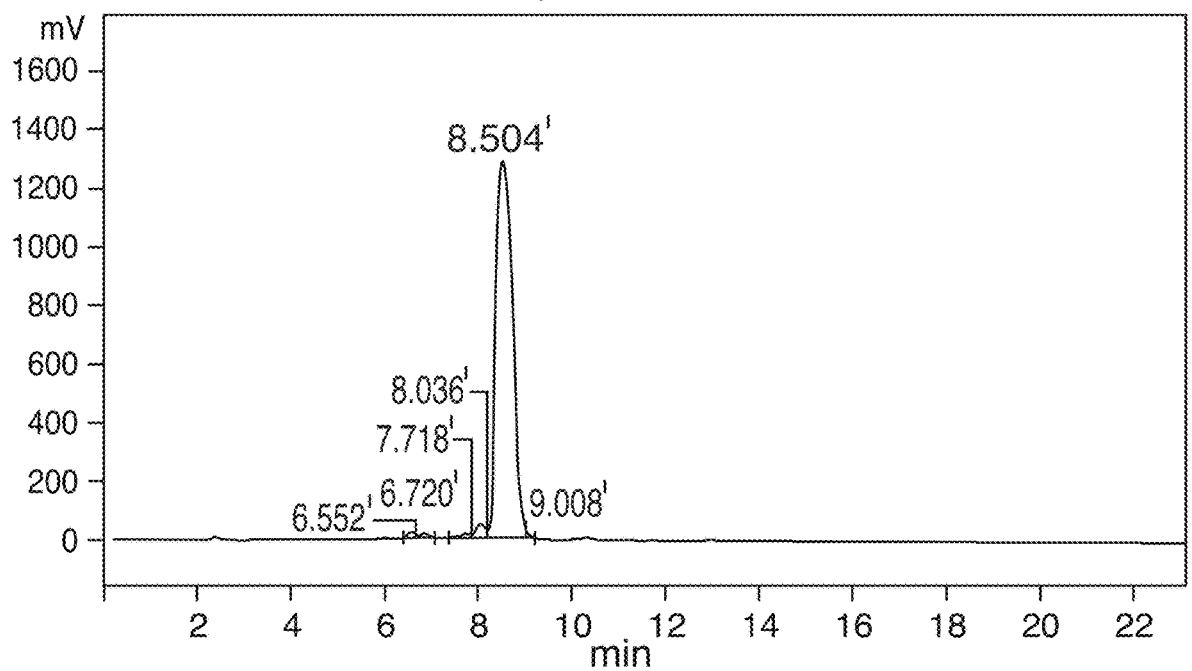
FIG. 7A and FIG. 7B show the HPLC and MS profiles of Control peptide #2.
Figure 7B:
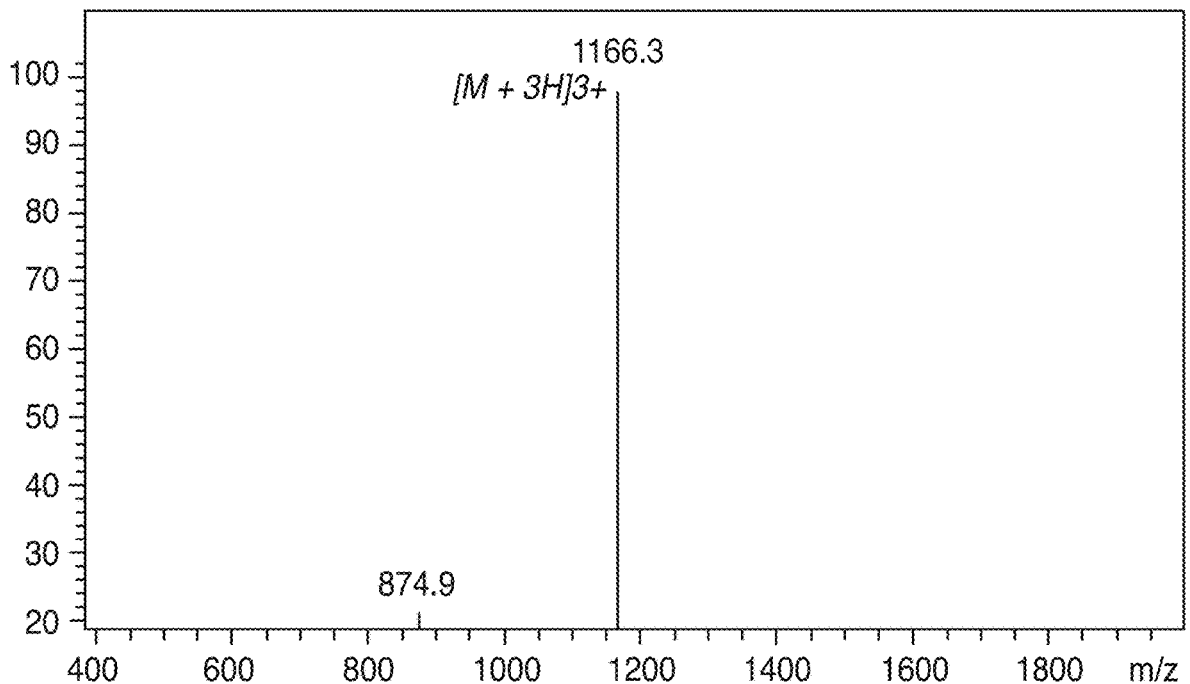

For some applications, the plurality of immunoglobulin molecules can be immobilized on a substrate (e.g., solid support) to facilitate subsequent handling and analysis. FIG. 2 shows a protein array 200. The protein array 200 includes a plurality of immunoglobulin molecules 205 as described in detail herein. The plurality of immunoglobulin molecules 205 are immobilized on a substrate 210 via a linker 215. The substrate 210 can be a porous or non-porous solid phase made from a material comprising polystyrene, polypropylene, polyvinylchloride, polyacrylamide, celluloses, dextrans, synthetic polymers, co-polymers, latex, silica, organosilica, agarose, metal, glass, or carbon, or a combination thereof. By way of example, the substrates can be constructed from materials such as, but not limited to, polymethylmethacrylate (LUCITE®, Lucite International, Southhampton, UK), ceramic, nitrocellulose, amorphous silicon carbide, polystyrene, and/or any other material suitable for microfabrication, microlithography, or casting. The substrate can include all or part of a surface of a microvolume plate, a pipet tip, a channel, a tube, a microtitre plate, a vial, a column or a polymeric bead. For example, the solid support can be a hydrophilic microtiter plate (e.g., MILLIPORE™, Millipore Corp., Billerica, Mass.) or a nitrocellulose-coated glass slide. Nitrocellulose-coated glass slides for making protein arrays are commercially available (e.g., from Schleicher & Schuell (Keene, N. H)).

The substrate 210 can also be a bead, such as a magnetic or agarose bead. In some embodiments, the bead is a polystyrene-coated magnetic bead. The substrate 210 can be coated with the immunoglobulin ligands described herein using any appropriate method. For example, the immunoglobulin molecules/ligands (e.g., vNARs) can be added to magnetic beads, for example, TALON® magnetic beads (commercially available from Invitrogen, USA), in a suitable buffer (such as PBS) and incubated for a period of time. The incubation can conveniently be carried out at room temperature whilst mixing on a rotary mixer. Before use, the beads can be washed, for example, three times with PBS buffer.

In some embodiments, the present technology provides a three dimensional porous membrane attached to a substrate such as glass with an inert polymer. Such a substrate typically includes multiple functional protein-specific binding sites. Such surfaces can be hydrophilic or hydrophobic. In some embodiments, the substrate is Protein slides I or Protein slides II (catalog numbers 25, 25B, 50, or 50B commercially available from Full Moon Biosystems, Sunnyvale, Calif.) In some embodiments, the substrate can be Protein slides II (cat. No. 25, 25B, 50, or 50B commercially avialble from Full Moon Biosystems). In some embodiments, the positionally addressable array of proteins utilize substrates such as UltraGAPS (Corning, Cat. No. 40015, commercially available from Corning Incorporated, Corning N.Y.), GAPS II (Corning, Cat. No. 40003, commercially available from Corning Incorporated, Corning N.Y.), Nickel Chelate-coated slides (commercially available, for example, from Greiner Bio-One Inc., Longwood, Fla. or from Xenopore, Hawthorne, N.J.), or Low Background Aldehyde slides (commercially available from Microsurfaces Inc., Minneapolis, Minn.). In some embodiments, the porous membrane can be coated with a magnetic layer. The three dimensional substrate can capture and protect captured antigens in the porous membrane. The porous membrane can have a thickness of greater than about 100 μm. In some embodiments, the porous membrane has a thickness of about 100-500 μm, or between about 100-250 μm. The pore size or the porous membrane can be any pore size conventionally used for biological materials, particularly peptides and polypeptides. In some embodiments, pore sizes can be as small as 50 Å and as large as 0.5 μm in diameter. These characteristics help maintain the morphology of the captured antigens. The antigens captured onto the substrate surface maintain their integrity, providing increased sensitivity and assay consistency.

In some embodiments, the immunoglobulin molecules 205 (e.g., vNARs) are immobilized on a functionalized glass substrate. This is particularly useful for embodiments that include methods for determining the presence of enzymatically active biomolecules. In some embodiments, a glass slide can be functionalized with an epoxy silane. The substrate 210 can have a silica or organosilica surface having a Maleimide polyethylene glycol (PEG) silane bonded to the silica or organosilica surface. The PEG repeat in such an embodiment can range from 3 to 300

The plurality of immunoglobulin molecules 205 can be immobilized in an array on a substrate 210. The resulting protein array can then be exposed to a biological sample from a chosen cell type or cell compartment, so that for those immunoglobulin molecules whose cognate protein antigens are present, binding occurs at the substrate. Binding can be assessed most conveniently by tagging the captured proteins (an antigen known to be present in the sample) with a readily detectable label, such as a fluorescent or other optically detectable chemical group, or a metal (in particular gold or silver) or a radiolabel, so that the presence of bound material is revealed by the accumulation of the tag in the array. The pattern of binding and the quantification of the bound material can be assessed particularly effectively where the array is immobilized on a substrate suitable for reading with an optical imaging device.

Methods of coupling biomolecules such as immunoglobulins to the substrate in an array are well known to those skilled in the art. An array format is convenient for analyzing a relatively large number of peptides rather than just a few peptides. Immobilization of the plurality of immunoglobulin molecules 205 on a solid surface/substrate (210) can be achieved through covalent coupling 215 or through non-covalent interactions (not shown). To this end, the immunoglobulin molecules can be derivatised with any suitable chemical groups, provided that this does not interfere with their binding capabilities. They can also be provided with a peptide extension through which coupling can conveniently be achieved. The constructs of the purified, recombinantly expressed igNAR derived binding domains are attached covalently to the above described substrates. Numerous types of reaction chemistry are employable to obtain this covalent linkage. In some embodiments, covalent linkage is afforded by reductive amination, NHS activated electrophilic substitution, carbodiimide dehydration or a Michael addition reaction. Silica or organosilica resin and surfaces can be activated using a single silane chemistry. Thus the covalent linkage is achieved by one or more processes selected from group consisting of a reductive amination, a NHS activated electrophilic substitution, a carbodiimide dehydration and a Michael addition reaction. In one example, acrylpropyltrimethoxysilane can be bonded to a silica surface and Michael addition chemistry can be used to covalently link the binding domain. Alternatively, a surface bonded silane can be reacted with bifunctional or heterofunctional molecules so as to afford surface reactive groups. An amino silane modified substrate can be combined with an NHS activated maleimide PEG to achieve the same end. As well, an amino silane modified substrate can be combined with bis-aldehyde reagents (such as glutaraldehyde or a PEG dialdehyde) and reductive amination to afford immobilizations that bridge the amine surface to the amine functional groups of the binding domain. Working from a silica or organosilica surface, silanes with longer spacers can be used. Maleimide polyethylene glycol (PEG) silane can be bonded on the surface and used for immobilization, wherein the PEG repeat can range from 3 to 300.

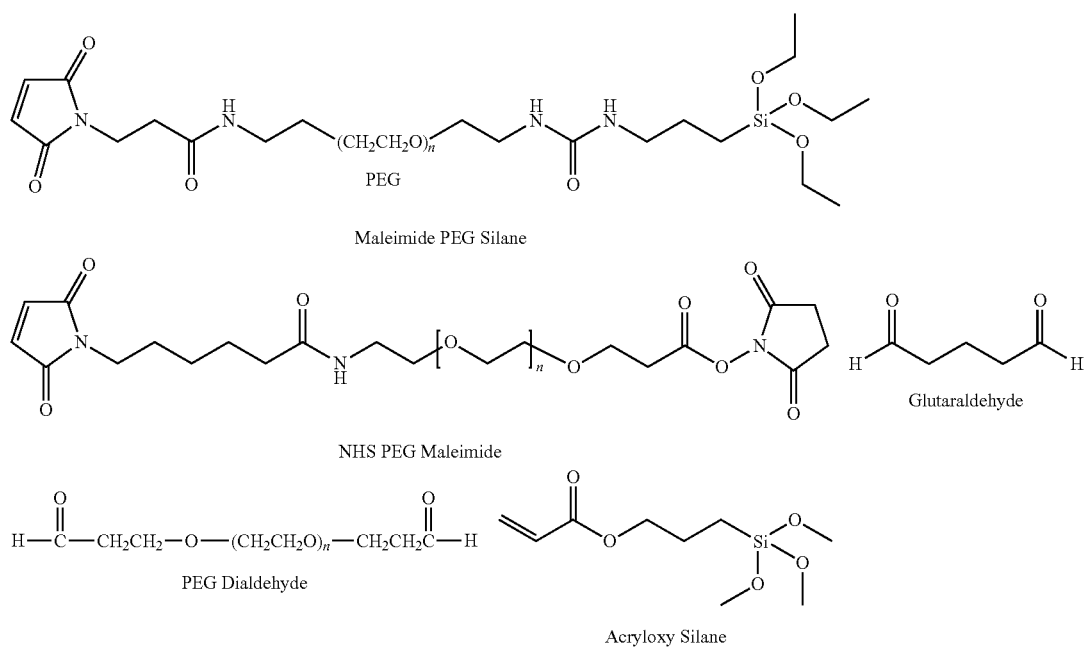

In some embodiments, polymeric materials and surfaces such as polypropylene or polystyrene are activated for covalent attachment using plasma treatment. In some cases the plasma treatment is followed by a solution chemistry step to bind the active groups on the surface and in other cases the plasma treated surface is used as-is. In some embodiments, polymerization of reactive groups is initiated on a polymeric surface, such as polystyrene divinylbenzene or polymethylmethacrylate, in a way to incorporate short or long spacer arm molecules for linking the binding domain to the substrate. For example, a binding domain containing a free thiol can be linked to a substrate using a maleimide containing PEG spacer. For some embodiments, the binding domain is incorporated into the polymer reaction products.

Accordingly, in some embodiments, the immunoglobulin molecules (e.g., vNARs) are bound directly to the substrate. The immunoglobulin molecules (e.g., vNARs) 205 can be bound to the substrate 210 via a linker 215. The linkage of the immunoglobulin molecules 205 to the substrate 210 can be via a cleavable or non-cleavable linker. In some embodiments, the immunoglobulin molecules (e.g., vNARs) 205 are attached to the substrate 210 via a His tag. The immunoglobulin molecules (e.g., vNARs) 205 can be attached to the substrate 210 via a 3-glycidooxypropyltrimethoxysilane ("GPTS") linker. The immunoglobulin molecules can be indirectly immobilized through biotinylation and the use of streptavidin residues or non-covalent adsorption to a hydrophobic surface. In some embodiments, the immunoglobulin molecules (e.g., vNARs) 205 are bound to the substrate 210 via biotin tags, wherein the substrate comprises a streptavidin-coated glass slide. The immunoglobulin molecules (e.g., vNARs) can be biotinylated at a specific site. In some embodiments, the specific site on the immunoglobulin molecules (e.g., vNARs) that is biotinylated is a BioEase tag (Invitrogen). In some embodiments, at least 2 tags are present on the on the immunoglobulin molecules, one of which can be used to aid in purification and the other can be used to aid in immobilization. The tag can be a His tag, a GST tag, or a biotin tag.

Captured Proteins and Antigens

The immunoglobulin molecules immobilized in the protein array can bind to its cognate binding partner in a substantially specific manner. Sequences of the immunoglobulin molecules with advantageous antigen binding specificity can be discovered by a multitude of techniques, including but not limited to, immunization of S. acanthias S. cirratus, G. cirratum, S. canicula, O. maculatus, T. scyllium, or C. plagiosum and phage display of library clones. Once discovered, the sequence of the IgNAR derived immunoglobulin molecules can be transformed into a gene and cloned into a plasmid through which recombinant expression can be performed. The gene and plasmid can be created so as to enable mammalian expression, to have a cleavable signal peptide, to have a poly Histidine affinity tag for facilitating purification, or to have an appendage sequence motif that can be used as a chemical handle for immobilization. Such a chemical handle can include an appended C-terminal cysteine residue or an azide-containing, unnatural amino acid residue. In addition, the template sequence and chemical handle of the IgNAR derived immunoglobulin molecules can be comprised of a linker amino acid sequence, including but not limited to QAPKVDAKFD. Although immunoglobulin molecules derived from shark single-domain heavy chain antibody lacking light-chains are exemplified herein, it is understood that the present arrays and methods described herein can be advantageously employed with other variants of the vNARs known to a person of skill in the art. Hence, the immunoglobulin molecules of the present technology specifically bind to proteins, including peptides, of any size or function. They can be intracellular proteins or extracellular proteins. They can be from a one-celled or multicellular organism. The organism can be a plant or an animal. In some embodiments, the cognate binding partners of the plurality of the immunoglobulin molecules in the protein array are human expression products, or fragments thereof.

In some embodiments, the cognate binding partners of the plurality of the immunoglobulin molecules can be a randomly chosen subset of all the proteins, including peptides, which are expressed by a mammalian cell, tissue or population of cells or a subset of all the fragments of those proteins. Thus, the cognate binding partners of the plurality of the immunoglobulin molecules represent a wide distribution of different proteins from a single organism (e.g., human). The cognate binding partners of the plurality of the immunoglobulin molecules need not necessarily be known. The cognate binding partners can be a protein (e.g., antibody) or peptide of unknown function. For example, the different immunoglobulin molecules of the array can together bind a wide range of cellular proteins from a single cell type, many of which are of unknown identity and/or function. The cognate binding partners of the plurality of the immunoglobulin molecules can be related proteins. The different proteins bound by the immunoglobulin molecules can optionally be members of the same protein family. The cognate binding partners of the plurality of the immunoglobulin molecules can be either functionally related or just be hypothesized of being functionally related. The different proteins bound by the immunoglobulin molecules of the array can also be proteins which share a similarity in structure or sequence or hypothesized of sharing a similarity in structure or sequence. By way of example, the cognate binding partners to the immunoglobulin molecules can optionally all be growth factor receptors, hormone receptors, neurotransmitter receptors, catecholamine receptors, amino acid derivative receptors, cytokine receptors, extracellular matrix receptors, antibodies, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators, small molecules and effectors, apoptosis-related factors, DNA synthesis factors DNA repair factors, DNA recombination factors, cell-surface antigens, hepatitis C virus (HCV) proteases or HIV proteases.

In some embodiments, the proteins which are the cognate binding partners of the plurality of the immunoglobulin molecules of the array can be fragments of the expression products of a cell or population of cells in an organism. The fragments include antibody fragments such as single-chain Fvs, Fab fragments, Fab' fragments, F(ab')2 fragments, Fv fragments, dsFvs diabodies, Fd fragments, fill-length, antigen-specific polyclonal antibodies, or even full-length monoclonal antibodies. In some embodiments, the plurality of the immunoglobulin molecules exhibit specificity for human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), or thyroglobulin and insulin. In some embodiments, the immunoglobulin molecules bind specifically to insulin like proteins, adeno-associated virus (capsid proteins 1, 2, 3), lentivirus, gamma retrovirus, anti-idiotypes of common IgG therapeutics, estrogen and progesterone receptors, human epidermal growth factor receptor 2 (HER2), E-Cadherin, pPDGFR and VEGFR, Akt, ERK, FAK, GSK3β, ILK, Integrin αV, PI3K, p38, PTEN and STAT3. In other embodiments, the immunoglobulin molecules bind specifically to mycotoxins or cytotoxins (e.g., emtansine). The cognate binding partners of the plurality of the immunoglobulin molecules of the array can be Fc domains of human antibodies. In some embodiments, the antibody fragments have unknown identity and/or function.

In some embodiments, the cognate binding partner could be a small (<1000 Da) molecule, such as a drug of abuse (including but not limited to methamphetamine, Anabolic steroids, cocaine, heroin, THC, oxycodone, hydrocodone, codeine, morphine and their biological metabolites) or a food toxin (including but not limited to aflatoxins, ochratoxins, and citrinin).

Methods of Using the Protein Arrays

Methods of using the protein arrays described herein, are exemplified for human proteins. However, it will be understood that the methods can be used for any mammalian species. The detection and quantification of proteins, peptides, monoclonal antibodies, and antibodies in complex samples play a critical role in functional analysis of biological systems, the detection of clinical diagnostic or prognostic biomarker proteins, and the identification of therapeutic targets. Patterns of protein profiles are also expected to become useful for the early detection, diagnosis and prognosis of a multitude of diseases, including cancer, auto immune, and congenital defects. Protein expression profiles provide vital information and facilitate the identification of new drug targets and the development of optimal structures and dosages for pharmacological reagents. The capture, isolation, harvesting and identification of proteins of interest from a complex biological sample, such as a biological medium that can contain various components such as proteins, nucleic acids, carbohydrates and small molecules, can be a challenging task. Methods for selectively enriching one or more proteins of interest can utilize the protein arrays described herein.

Accordingly, the present technology provides a method for determining the presence of one or more proteins of interest in a sample. The method includes contacting a sample having one or more proteins of interest with a protein array having a plurality of immunoglobulin molecules (for example, the protein arrays and embodiments thereof described herein) under conditions suitable for binding of the one or more proteins of interest to the plurality of immunoglobulin molecules of the protein array. The method also includes capturing the one or more proteins of interest with the protein array wherein the at least one variable antigen-binding domain of the plurality of immunoglobulin molecules of the protein array binds specifically to the one or more proteins of interest. The method also includes eluting the captured one or more proteins of interest with a solvent and detecting the presence of the one or more proteins of interest. In some embodiments, the proteins of interest are selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, and insulin.

Some embodiments, the technology relates to the capture of targets using protein arrays comprising binding domains derived igNARs. Such targets can include biomarkers. In some embodiments, biomarkers are useful to determine a diagnosis and/or prognosis for a disease or disorder. In some embodiments, one or more markers can be used in the diagnosis and/or prognosis of a disease or disorder. Examples of diseases and disorders include cancer, such as prostate cancer, ovarian cancer, liver cancer, testicular cancer, pancreatic cancer, colon cancer, breast cancer. More examples include Alzheimer's disease, brain trauma, such as chronic traumatic encephalopathy (CTE), gastrointestinal stromal tumor, and viral and non-viral infections.

In some embodiments, the methods provided herein can include passing a biological sample comprising a relatively low concentration of one or more proteins of interest through at least one protein array described herein. The analyte of interest might be present in the biological sample at a concentration as high as 100 µg/mL but also as low as 1 picogram/mL. In such embodiments, a column, or processing chamber, having a hollow interior can be provided that includes the protein array within the hollow interior. For example, the protein array can be a stationary phase within a chromatographic column. In some embodiments, the protein array can be packed into a pipette tip or coated onto surfaces of microvolume plates or other sample preparation devices (e.g., vials). The biological sample can be flowed over the protein array. The proteins of interest can be selectively captured on the protein array and later eluted from the protein array for analysis and/or detection.

Conditions suitable for binding of the one or more proteins of interest to the plurality of immunoglobulin molecules of the protein array depends of the specific proteins that can be optimized using routine molecular biology techniques known to a person of skill in the art. In many embodiments, it is suitable to directly subject an unadulterated biological to the protein array. In other embodiments, the sample can be buffer exchanged or diluted into a buffer condition that optimizes binding capacity, including but not limited to buffers with physiologically relevant properties. Phosphate, borate, ammonium, triethanolamine, MES, HEPES, Tris, bis-tris propane buffered solutions can be effectively used as diluents. Methods can further include selectively enriching the proteins of interest by altering the binding affinity of the immunoglobulin molecules described herein to the proteins of interest. In some embodiments, at least one variable antigen-binding domain of the plurality of immunoglobulin molecules of the protein array binds specifically to the one or more proteins of interest with a dissociation constant ($K_D$) of $1 \times 10^{-6}$ M or less. In other embodiments, at least one variable antigen-binding domain of the plurality of immunoglobulin molecules binds specifically to the one or more proteins of interest with a $K_D$ of at least $1 \times 10^{-7}$ M, at least $1 \times 10^{-8}$ M, at least $1 \times 10^{-9}$ M, at least $1 \times 10^{-10}$ M or at least $1 \times 10^{-12}$ M.

One or more protein of interest bound to the protein array described herein can be characterized by an enzyme linked immunosorbent assay (ELISA). In vitro tests for detection of one or more proteins bound to the protein array described herein are mostly based on the ELISA principle, where an immunoglobulin molecule (e.g., one of the vNAR with SEQ ID NOIS 2-5) is immobilized onto a solid phase, which is then incubated with a sample, and after washing off the non-bound sample, the specifically bound proteins are detected with a secondary antibody or an affinity binder of sorts generating a detectable signal known to those skilled in the art (color, photons, etc). One or more of the proteins of interest captured by the protein array can be determined by an ELISA. Detection of the one or more proteins of interest bound to the protein array can depend on incorporation of a label molecule (such as a QNP) and identification of the positive array element. Incorporation of the reporter molecule (e.g., a fluorescent tag) into the protein of interest (prior to performing the assay) or by indirect labeling of the protein of interest with another molecule (typically an antibody or antibody fragment) can facilitate accurate detection and quantification. An alternative approach can be analysis by western blot and immunohistochemistry.

Functional testing (e.g., binding affinity to select proteins that is known to be functional) of the one or more proteins of interest captured by the protein array can be performed and the results compared against available reference tests or against available standard preparations. The binding affinity can also be determined by various methods known in the art. For example, the protein sample eluted from the protein array can be used for an ELISA assay to determine protein content, or can be tested on a 1D or 2D protein gel, whereby not only the total protein content of the antigens bound to the protein array can be estimated, but also the nature of the unbound proteins (those which are no longer present on the gel) can be documented by looking at the size/position of the protein peaks or dots.

In some embodiments, the ELISA assay is performed in combination with detection based on mass spectrometry. Alternatively, the protein array can be used solely for sample enrichment and quantitation of the analyte(s) can be readily performed by mass spectrometry or mass spectrometry used in conjunction with liquid chromatography or capillary electrophoresis. Mass spectrometry can achieve the sensitivity, robustness and sample throughput that allow the identification and accurate quantification of the protein of interest. In some embodiments, one or more of the proteins of interest captured by the protein array described herein is determined by a combination of an ELISA and mass spectrometry analysis. In some embodiments, one or more of the proteins of interest captured by the protein array described herein is determined by a bead assay. Bead assays are especially suited for determining the presence of protein of interest in a smaller volume of sample material. Beads can be coded by using various concentrations of fluorescent dye, or by some type of barcoding technology such as size of the bead. Consequently, bead assays can easily be multiplexed. In some instances, magnetic beads can efficiently be functionalized using a biotin-based sdAb immobilization. This approach can be the method of choice for the development of cost-efficient protein array based detection for diagnostic purposes.

The protein analysis methods described herein can provide information as to the levels and distribution of the proteins in a specific sample (e.g., human tissue). The function or location of a subset of proteins can also be examined by the assays described herein.

One aspect of the present technology provides a method of comparing the protein expression patterns of two samples. The method includes the step of contacting a first sample and a second sample comprising one or more proteins of interest with the protein array described herein (including a plurality of shark immunoglobulin molecules) under conditions suitable for binding the one or more proteins of interest to the protein array. The method also includes detecting the amount of protein from the first and the second sample, respectively, bound to the protein array, and comparing the amounts of protein from the first and the second sample, respectively, bound to the protein array. In some embodiments, the method is performed in two different protein arrays. In some embodiments, the proteins of interest are selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, and insulin. The expression levels and/or pattern of the one or more of the proteins of interest captured by the protein array from the first and the second samples, respectively, can be determined by an ELISA. In some embodiments, the expression levels and/or pattern of the one or more of the proteins of interest captured by the protein array from the first and the second samples, respectively, is determined by an ELISA in combination with mass spectrometry. The first sample and the second sample can be two mammalian cells or a population of two mammalian cells.

In another aspect, the technology relates to a method for enrichment or purification of one or more proteins of interest in a sample. The method includes the steps of contacting a sample comprising one or more proteins of interest with the protein array comprising a plurality of immunoglobulin molecules (e.g., the protein arrays described herein) under conditions suitable for binding of the one or more proteins of interest to the plurality of immunoglobulin molecules of the protein array. The method also includes capturing the one or more proteins of interest with the protein array wherein the at least one variable antigen-binding domain of the plurality of immunoglobulin molecules of the protein array binds specifically to the one or more proteins of interest. The method also includes eluting the captured one or more proteins of interest with a solvent and determining the purity of the one or more proteins of interest.

In some embodiments, the proteins of interest are selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, and insulin. The enrichment levels and/or the purity of the one or more of the proteins of interest captured by the protein array can be determined by an ELISA. In some embodiments, the enrichment levels and/or the purity of the one or more of the proteins of interest captured by the protein array is determined by an ELISA in combination with mass spectrometry. In some embodiments, determining the purity comprises measuring the functionalities of one or more proteins of interest. For example, a sample purified by the protein array can be tested for enzymatic activity by a cell based assay or in vitro assay. A sample purified by the protein array can also be tested for its affinity to interact with another molecule, in which case an interferometry or surface plasmon resonance analysis could be performed. The methods for selectively enriching of one or more proteins of interest can include selectively enriching particular types of proteins. Examples of the types of proteins that can be selectively enriched using the methods described herein can include biomarkers, enzymes, scaffolding proteins, immunoglobulins and the like. More examples include proteins associated with a particular disease or disorder, such as Cancer, diabetes, Alzheimer's disease, chronic traumatic encephalopathy (CTE), and an infection e.g. viral and non-viral infection. Proteins can be associated with a particular type of cancer, and/or particular stage of a disease or disorder, such as particular stage of a cancer.

Another aspect of the technology provides a method of evaluating a disease condition in a tissue in an organism. The method includes the steps of contacting a diseased tissue in an organism comprising one or more proteins of interest with the protein array under conditions suitable for binding of the one or more proteins of interest to the plurality of immunoglobulin molecules of the protein array. The method also includes capturing the one or more proteins of interest with the protein array wherein the at least one variable antigen-binding domain of the plurality of immunoglobulin molecules of the protein array binds specifically to the one or more proteins of interest. The method also includes detecting the presence of one or more proteins of interest and comparing the expression of the one or more proteins of interest in the diseased tissue with a corresponding expression in a healthy or normal tissue or a control sample. The altered expression and/or absence of expression of the protein of interest in the diseased tissue is indicative of the disease condition. The terms "normal" and "healthy" are used herein interchangeably. They refer to tissue samples from individuals or group of individuals (e.g., human subjects) who have not shown any symptoms of the diseased state (e.g., cancer) and have not been diagnosed with the disease. The normal tissue can be obtained from an individual (or group of individuals) who is not on medication for the disease and has not been diagnosed with any other disease. In some embodiments, tissue samples are obtained from normal individuals having similar sex, age, body mass index as compared with the individual from whom the diseased tissue sample was obtained. The term "normal" is also used herein to qualify a sample isolated from a healthy individual. In the context of the above described embodiment of the present technology, the terms "control sample," and "reference sample," refer to the biological sample(s) isolated from an individual or group of individuals that are normal (i.e., healthy). A control sample can also refer to a biological sample isolated from a patient or group of patients diagnosed with a specific disease subtype (e.g., pancreatic cancer) or a specific stage of the disease (e.g., early or stage IV). The term "control sample" (or "control") can also refer to the compilation of data derived from samples of one or more individuals classified as normal, or one or more individuals diagnosed with disease, a specific disease subtype or a specific stage of disease, or one or more individuals having undergone treatment for the disease.

Information on expression levels of a given set of biomarkers obtained using biological samples from individuals afflicted with a particular stage of the disease (e.g., healthy subjects, patients with diabetes, with subtype of type II, with early pre-diabetic disease, or with late diabetes) can be grouped to form a disease expression profile map. The disease expression profile map results from the study of a large number of samples obtained from individuals with the same disease stage/status/subtype. In some embodiments, the disease expression profile map is established using samples from individuals with matched age, sex, and body index. Each expression profile map provides a template for comparison to biomarker expression patterns generated from unknown biological samples. As will be appreciated by those of ordinary skill in the art, sets of biomarkers whose expression profiles correlate with disease, can distinguish between different subtypes of the disease and/or can discriminate between different stages of the disease can be used to identify, study or characterize unknown biological samples. Accordingly, the present technology provides methods for characterizing biological samples obtained from a subject suspected of having the disease, for diagnosing disease in a subject, for identifying the subtype of disease, and for assessing the advancement of disease in a subject. In such methods, the biomarkers' expression levels determined for a biological sample obtained from the subject are compared to the levels in one or more control samples.

In some embodiments, the proteins of interest in a sample from a diseased tissue is selected from a group consisting of human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, and insulin. In some embodiments, the detection and/or characterization of the one or more of the proteins of interest captured by the protein array is determined by an ELISA. The detection and/or characterization of the proteins of interest captured by the protein array can be determined by an ELISA in combination with mass spectrometry. In some embodiments, the disease condition is selected from a group consisting of a cancer, a type I diabetes, a type II diabetes, an immunomodulatory disease, an autoimmune disease, an inflammatory disease, an endocrinal disease, a pulmonary disease, a hepatic disease, a cardiovascular disease, and a neurodegenerative disease.

Vectors and Cells Comprising Vectors

The disclosure provides vectors and methods for vector-mediated delivery and expression of shark single-domain heavy chain antibody (shark sdAbs) that are effective in the treatment of a disease condition selected from a group consisting of a cancer, a type I diabetes, a type II diabetes, an immunomodulatory disease, an autoimmune disease, an inflammatory disease, an endocrinal disease, a pulmonary disease, a hepatic disease, a cardiovascular disease, and a neurodegenerative disease. In particular, the disclosure relates to the use of recombinant viral and non-viral vectors to deliver shark sdAbs that inactivate one or more genes causing a disease condition. Exemplary vectors include but are not limited to, viral and non-viral vectors, such as retroviruses (including lentiviruses), adenovirus (Ad) vectors including replication competent, replication deficient and gutless forms thereof, adeno-associated virus (AAV) vectors, simian virus 40 (SV-40) vectors, bovine papilloma virus vectors, Epstein-Barr virus vectors, herpes virus vectors, vaccinia virus vectors, Moloney murine leukemia virus vectors, Harvey murine sarcoma virus vectors, murine mammary tumor virus vectors, Rous sarcoma virus vectors and nonviral plasmid vectors. In one preferred approach, the vector is a viral vector. Viruses can efficiently transduce cells and introduce their own DNA into a host cell. In generating recombinant viral vectors, non-essential genes are typically replaced with a gene or coding sequence for a heterologous (or non-native) protein such as the shark sdAbs.

Adenovirus gene therapy vectors are known to exhibit strong expression in vitro, excellent titer, and the ability to transduce dividing and non-dividing cells in vivo (Hitt et al., Adv in Virus Res 55:479-505 (2000)). When used in vivo these vectors lead to strong but transient gene expression due to immune responses elicited to the vector backbone. A therapeutic compound-encoding gene (e.g the polynucleotide encoding the shark sdAbs described herein) is commonly inserted into adenovirus in the deleted E1A, E1B or E3 region of the virus genome. In some embodiments, the adenoviral vectors for use in practicing the disclosure do not express one or more wild-type Ad gene products, e.g., E1a, E1b, E2, E3, E4. In specific embodiments, the virions are typically used together with packaging cell lines that complement the functions of E1, E2A, E4 and optionally the E3 gene regions. See, e.g. U.S. Pat. Nos. 5,872,005, 5,994, 106, 6,133,028 and 6,127,175, expressly incorporated by reference herein in their entirety. Adenovirus vectors are purified and formulated using standard techniques known in the art.

The present disclosure provides a variant AAV capsid protein, where the variant AAV capsid protein comprises an insertion of from about 5 amino acids to about 11 amino acids in an insertion site in the capsid protein GH loop or loop IV, relative to a corresponding parental AAV capsid protein, and where the variant capsid protein, when present in an AAV virion. confers increased infectivity of target cells by an AAV virion comprising the corresponding parental AAV capsid protein. In some embodiments, the AAV vector can include a capsid, which influences the tropism/targeting, speed of expression and possible immune response. The vector can also include the rAAV, which genome carries the transgene/therapeutic aspects (e.g., sequences encoding shark sdAbs) along with regulatory sequences. The term "rAAV" refers to a "recombinant AAV". In some embodiments, a recombinant AAV has an AAV genome in which part or all of the rep and cap genes have been replaced with heterologous sequences. In some embodiments, the vector can include the targeting sequence within/on a substrate that is or transports the desired molecule (therapeutic molecule, diagnostic molecule, etc.). In some embodiments, the sequence of shark sdAb is part of a capsid protein of the AAV vector. In some embodiments, the sequence of shark sdAb is inserted between specific regions (e.g., AA588-589) of an AAV sequence of the vector rAAV virions for use in practicing the present disclosure may be produced using standard methodology, known to those of skill in the art and are constructed such that they include, as operatively linked components in the direction of transcription, control sequences including transcriptional initiation and termination sequences, and the coding sequence for a therapeutic compound or biologically active fragment thereof. Particularly, methods are known in the art for generating rAAV virions: AAV vector and AAV helper sequences, e.g., with co-infection with one AAV helper virus (e.g., adenovirus, herpesvirus, or vaccinia virus) Transfection with or transfection without recombinant AAV vectors, AAV helper vectors, and accessory function vectors. Non-limiting methods for generating rAAV virions include, for example, U.S. Pat. Nos. 6,001,650 and 6,004,797, international applications PCT/US16/64414 (published as WO 2017/096039) and U.S. Provisional Patent Application Nos. 62/516,432 and 62/531,626. Following recombinant rAAV vector production (i.e, vector production in cell culture systems), rAAV virions can be obtained from host cells and cell culture supernatants and purified. Exemplary AAV vectors are vectors derived from an adeno-associated virus serotype, including without limitation, AAV-1, AAV-2, AAV-3, AAV-4, AAV-5, AAV-6, AAV-7, AAV-8, etc.

In some embodiments, a capsid library is provided that comprises AAV genomes that contain both the full rep and cap sequence that have been modified so as to not prevent the replication of the virus under conditions in which it could normally replicate (co-infection of a mammalian cell along with a helper virus such as adenovirus). In some embodiments, the system could be used to develop capsids that exhibit enhanced targeting of specific cells/organs, select for capsids that evade immunity, select for genomes that are more at homologous recombination, select for genome elements that increase the efficiency of conversion of the single stranded AAV genome to a double stranded DNA genome within a cell and/or select for genome elements that increase the conversion of AAV genome to a persistent, circularized form within the cell.

The disclosure provides methods of isolating a population of recombinant adeno-associated virus (rAAV) particles of any capsid serotype from in-process impurities by capturing the rAAV particles on media selected from an apatite chromatography medium and magnetic beads. The methods of the disclosure entail upstream processing (such as, for example, centrifugation, treatment with Benzonase® (available from MilliporeSigma, Burlington, Mass.), anion exchange filtration, and/or tangential flow filtration) as well as downstream processing (such as, for example, heat inactivation, filtration, hydrophobic interaction chromatography, size exclusion chromatography, and/or anion exchange chromatography). The upstream and downstream methods may be used alone or in various combinations. Optionally, a further step to clear trace contaminants, such as adventitious viruses which may be present in the feedstream, can be incorporated into the process, thereby yielding a commercially reasonable orthogonal process. Thus, in some embodiments, the process further includes a viral clearance filter. Examples of such filters are known in the art and include Viresolve® NFR (50 nm) (available from MilliporeSigma, Burlington, Mass.), Ultipor® VF (50 nm) (available from Pall Corporation, Port Washington, N.Y.), and Asahi 70 nm. The present disclosure also provides methods that can resolve an empty genome-free, partial genome-containing, and full genome-packaging virus particles as well as contaminants such as capsid fragments and genomes.

The present disclosure also provides vectors comprising a polynucleotide encoding a IgNAR variable domain according to the present disclosure. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal ($\Psi$), a primer binding site (PBS), one or more (e.g., two) long terminal repeats (LTR), and a transgene of interest, e.g., a gene encoding a CAR comprising shark sdAbs. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 Jun.; 3(6): 677-713.

The present disclosure further provides a host cell comprising one or more vectors of the disclosure. Polynucleotides encoding a IgNAR variable domain (e.g., vNAR) of the disclosure can be incorporated into a recombinant replicable vector (e.g., viral vectors). The vector may be used to replicate the nucleic acid in a compatible host cell. The vectors may be, for example, plasmid, phagemid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampicillin, methotrexate, tetracycline, neomycin (Southern et al., J., J Mol Appl Genet. 1982; 1(4):327-41 (1982)), mycophenolic acid (Mulligan et al., Science 209:1422-7 (1980)), puromycin, zeomycin, hygromycin (Sugden et al., Mol Cell Biol. 5(2):410-3 (1985)) or G418.

In another embodiment, the vector comprising the nucleic acid encoding the desired CAR of the disclosure is an adenoviral vector (e.g., A5/35). In another embodiment, the expression of nucleic acids encoding CARs can be accomplished using of transposons such as sleeping beauty, crisper, CAS9, and zinc finger nucleases. See below June et al. 2009 Nature Reviews Immunology 9.10: 704-716, is incorporated herein by reference.

In another embodiment, the vector comprising the nucleic acid encoding the desired CAR of the disclosure is a retroviral transfer vectors comprising one or more transgene sequences (e.g. transgene encoding shark sdAbs) and retroviral packaging vectors comprising one or more packaging elements. The core sequence of the retroviral vectors of the present disclosure may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present disclosure includes, but is not limited to, lentivirus. Other retroviruses suitable for use in the compositions and methods of the present disclosure include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Administration of Gene Therapy vectors

Typically, vectors are included in a packaging cell, and are introduced into the cell via transfection, transduction or infection. Methods for transfection, transduction or infection are well known by those of skill in the art. A retroviral transfer vector of the present disclosure can be introduced into a packaging cell line, via transfection, transduction or infection, to generate a producer cell or cell line. The packaging vectors of the present disclosure can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880 Zufferey et al., 1997, Nature Biotechnology 15:871-875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used. The packaging vectors of interest may contain additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

The gene therapy vectors and constructs described above may be introduced into cells using standard methodology known in the art. Such techniques include transfection using calcium phosphate, micro-injection into cultured cells (Capecchi, Cell 22:479-488 [1980]), electroporation (Shigekawa et al., BioTechn., 6:742-751 [1988]), liposome-mediated gene transfer (Mannino et al., BioTechn., 6:682-690 [1988]), lipid-mediated transduction (Felgner et al., Proc. Natl. Acad. Sci. USA 84:7413-7417 [1987]), and nucleic acid delivery using high-velocity microprojectiles (Klein et al., Nature 327:70-73 [1987]).

The disclosure contemplates administration of the recombinant vectors to a patient with disease condition in order to slow or completely cure the disease. The disease condition is selected from a group consisting of a cancer, a type I diabetes, a type II diabetes, an immunomodulatory disease, an autoimmune disease, an inflammatory disease, an endocrinal disease, a pulmonary disease, a hepatic disease, a cardiovascular disease, and a neurodegenerative disease. Administration to the patient may be by any known method, including both in vivo and ex vivo modes of administration.

In vivo delivery involves delivery of a gene therapy vector of the disclosure directly to a patient. In some cases, the vector is delivered to a depot organ, e.g., liver or muscle, by intraportal (IP) or intramuscular (IM) injection, respectively that generates and secretes the transgene product of interest. In other approaches, the vector is delivered intravenously (IV). Such delivery may also be by the intraperitoneal route or by delivery directly to the tumor site. Convection-enhanced delivery to the brain is also contemplated. Non-invasive methods, such as oral delivery, are also contemplated. In some cases, delivery may be accomplished by an ex vivo route. Ex vivo delivery involves ex vivo (outside the body) transduction of cells by the recombinant vectors, followed by administration of the transduced cells to the patient.

The gene therapy vectors of the disclosure are delivered in an amount effective yield to a therapeutic level of the therapeutic factor or factors encoded by the vector(s) in the vicinity of cancer cells or a tumor.

The present disclosure contemplates treatment regimens that include the use of gene therapy vectors that encode a shark sdAb, alone or in combination with one or more additional therapeutic compounds and may further include any of a number of modes of therapeutic intervention typically employed by those of skill in the art to treat the type of disease under therapy.

Methods of Stem Cell Gene Therapy

Methods of the present disclosure include administering a population of genetically modified stem cells to a patient suffering from a condition that results from a defective gene (e.g., a mutation). Generally, the present methods relate to stem cell gene therapy, in which the genome of living cells (e.g., stem cells) is modified for therapeutic purposes. In particular, a therapeutic effect can be achieved by correcting a defective gene, as described herein. By way of example, haematopoietic stem cell (HSCs) may be extracted from a patient suffering from a disorder caused by the defective gene (e.g., a sickle cell patient with a defective HBB gene) and purified by selecting for CD34 expressing cells (CD34+). The isolated cells can be treated ex vivo using known methods in the art (e.g., using CRISPR-Cas 9 system), and its genome can be modified as desired, e.g., edited to correct the defective target gene into a functional gene. Such modified stem cells are subsequently administered back to the patient. The transplanted stem cells take root in the patient's bone marrow, replicating and creating cells that mature and create normally functioning protein, thereby resolving the problem.

Methods of isolating stem cells from a source and further treatment of the cells ex vivo (e.g., expansion and genome modification) are well known and available in the art. In some embodiments, the stem cells are allogeneic to the mammal to which they are administered. In some embodiments, the stem cells are autologous to the mammal to which they are administered.

The genetically modified cells described herein may be used in genetically modified stem cell therapy, or stem cell gene therapy, which refers to the in vitro gene editing (e.g., by CRISPR/Cas system or by retroviral transduction) of cells to form genetically modified cells prior to introducing into a patient. Therefore, the genetically modified stem cells described herein are used in methods of gene therapy because they contain the altered or corrected gene. In particular, the genetically modified stem cells described herein are useful in methods of gene therapy because all or most progeny from the modified stem cells will contain the altered or corrected gene. The modified cells can therefore be used for treatment of a mammalian subject, such as a human subject, suffering from a disease condition selected from a group consisting of a cancer, a type I diabetes, a type II diabetes, an immunomodulatory disease, an autoimmune disease, an inflammatory disease, an endocrinal disease, a pulmonary disease, a hepatic disease, a cardiovascular disease, and a neurodegenerative disease.

The present disclosure includes retroviral and lentiviral vector constructs expressing a "Chimeric Antigen Receptor" that can be directly transduced into a cell. The CARs can include an antigen binding domain comprising shark sdAbs. In some embodiments, methods of the present disclosure include administering a population of chimeric antigen receptor T-cell (CART) comprising the shark sdAbs. "Chimeric Antigen Receptor" or alternatively a "CAR" as the term is used herein, refers to a recombinant polypeptide construct comprising at least an extracellular antigen binding domain (e.g., shark sdAbs), a transmembrane domain and a cytoplasmic signaling domain comprising a functional signaling domain derived from a stimulatory molecule and/or costimulatory molecule as defined below. In some embodiments, the CARs provided herein comprise an extracellular antigen binding domain with an amino acid sequence that is 100% identical to the amino acid sequence set forth in any one of the four sequences, 4HGK (SEQ ID NO.2), 2COQ (SEQ ID NO.3), 1SQ2 (SEQ ID NO.4) and 2125 (SEQ ID NO.5). In other embodiments, the CARs provided herein comprise an extracellular antigen binding domain with an amino acid sequence that is at least 80%, at least 85%, at least 90%, at least 95%, at least 98%, or at least 99%, identical to any one of the four sequences, 4HGK (SEQ ID NO.2), 2COQ (SEQ ID NO.3), 1SQ2 (SEQ ID NO.4) and 2125 (SEQ ID NO.5). In some embodiments, the domains in the CAR polypeptide construct are in the same polypeptide chain, e.g., comprise a chimeric fusion protein. In other embodiments, the domains in the CAR polypeptide construct are not contiguous with each other, e.g., are in different polypeptide chains.

Kits and Diagnostic Devices

In another aspect, the technology relates to kits and diagnostic devices comprising materials useful for carrying out diagnostic methods according to the present technology. The diagnosis/characterization/staging procedures described herein can be performed by diagnostic laboratories, experimental laboratories, or practitioners. The technology provides kits which can be used in these different settings.

The diagnostic devices include at least one protein array of the present technology that is used for the determination of expression levels of a plurality (i.e., one or more, e.g., at least 2, at least 3, at least 4, at least 5, at least 6, at least 7, at least 8, at least 9, at least 10 or more) of polypeptides in a biological sample obtained from a subject. Determination of protein expression levels in the practice of the inventive methods can be performed by any suitable method (see, for example, E. Harlow and A. Lane, "Antibodies: A Laboratories Manual", 1988, Cold Spring Harbor Laboratory: Cold Spring Harbor, N.Y.). Protein expression levels can be determined using the diagnostic devices of the present technology in conjunction with conventional immunoassays know in the field. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay can be competitive or non-competitive. Methods of detection and quantification of the signal generated by the binding of the protein of interest to the binding domain of the immobilized immunoglobulin molecule can depend on the nature of the assay and of the detectable moiety (e.g., fluorescent moiety). Protein expression levels can also be determined using mass spectrometry based methods or image (including use of labeled ligand) based methods known in the art for the detection of proteins. Other suitable methods include proteomics-based methods.

Materials and reagents for characterizing biological samples, diagnosing disease in a sample, identifying disease subtype, and/or identifying disease stage in a sample according to the methods described herein can be assembled together in a kit. The kit includes at least one protein array that specifically detects expression levels of one or more inventive biomarkers, and instructions for using the kit according to a method described herein. Each kit can include a protein array with a known sequence of immunoglobulin molecules which renders the procedure specific. For detecting/quantifying a protein biomarker (or an analog or fragment thereof), the immunoglobulin molecules derived from igNARs that specifically detects expression levels of the biomarker specifically binds to the biomarker (or analog or fragment thereof). In some embodiments, the immunoglobulin molecules derived from igNARs are immobilized on a substrate surface (e.g., beads, an array, and the like).

Depending on the procedure, the kit can also include one or more of: extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure can be included in the kit. The reagents can be supplied in a solid (e.g., lyophilized) or liquid form or as a protein chip. The kits can also include different containers (e.g., vial, ampoule, test tube, flask or bottle) for each individual buffer and/or reagent. Each component can generally be suitable as aliquoted in its respective container or provided in a concentrated form. Other containers suitable for conducting certain steps of the disclosed methods can also be provided.

In some embodiments, the kits also include control samples. The kits can include at least one expression profile map for a particular disease, disease subtype, and/or disease progression as described herein for use as comparison template. The expression profile map can be digital information stored in a computer-readable medium.

Instructions for using the kit according to one or more methods of the technology can include instructions for processing the biological sample obtained from the subject and/or for performing the test, instructions for interpreting the results as well as a notice in the form prescribed by a governmental agency (e.g., FDA) regulating the manufacture, use or sale of pharmaceuticals or biological products.

In some embodiments, the kits include a sample preparation device (e.g., a pipette, microvolume plate, tubes, sample vials, or other labware) that includes (e.g., is packed with or coated with) the protein array described herein. The kit can also include instructions for use with any of the methods described herein. In some embodiments, the kit includes a column for use in chromatography. The column includes the protein array as the stationary phase inside the column.

All patent and literature references cited in the present specification are hereby incorporated by reference in their entirety.

EXAMPLES

The below Examples further describe and demonstrate the compositions of the present disclosure and their uses. The Examples are not intended to limit the disclosure in any way. Unless described in the past tense, descriptions of experiments are not intended to convey that the experiments have actually been performed.

The present Examples describe, among other things, experiments in cells such as cultured cells. However, one of ordinary skill in the art reading the present specification will understand that the present specification also teaches application of the disclosed compositions and methods, in a therapeutic context, for example, in mammalian tissue (e.g., pancreatic tissue) and/or in a subject (e.g., a subject with type 2 diabetes), as described further herein.

Example 1: Method for Producing Immunoglobulin Molecules Derived from Shark igNARs This Example illustrates a method that can be employed to produce immunoglobulin molecules derived from shark igNARs. Methods that can be used for cloning, expression, and purification of the shark igNAR variable domain (vNAR) peptides, are provided herein.

a) Library Construction

Primary libraries based on wild-type Wobbegong igNAR protein variable domain fragment having wild-type and mutants can be made. The mutations can be in the framework regions or in the CDR3 loop regions in the CDR3 region (i.e. between Tyr85 and Lys97) of the wild-type sequence. Precautions to reduce the chance of introducing hydrophobic patches (typical of "sticky" or non-specific clones) will be taken to allow subsequent step-wise maturation of lead molecules. To create the libraries, for example, all randomized amino acid positions between Tyr and Lys in the CDR3 region can be encoded in the library by an NNK codon (where N represents an equal mix of G, A, T and C;

and K represents an equal mix of G and T) in the nucleic acid sequence. Libraries can be PCR-generated using a GeneArt synthesised Wobbegong igNAR variable domain scaffold, and cloned as digested fragments into similarly digested vector.

To construct libraries in the NAR variable region for the phage display, two groups (5 sharks each) of sharks (*Chiloscyllium plagiosum*, that have not been immunized before) were immunized with 4-week interval via tail vein injection strategy with the chemically synthesized target antigen. Target protein and/or target peptide of interest were chemically synthesized by conventional methods know to a person of skill in the art. The synthesized target protein/peptide and the control peptides were conjugated with either biotin or KLH (keyhole limpet hemocyanin). Sharks in group 1 were injected with peptide target with an amino acid sequence as set forth in SEQ ID NO. 7 and sharks in group 2 were injected with a complex of peptide and protein targets. amino acid sequence as set forth in SEQ ID NO. 7 and Group 2 was injected with a complex of peptide and protein targets. The quality of the synthetic peptides shown in Table 1 below were detected by high performance liquid chromatography (HPLC) and mass spectrometry (MS).

TABLE 1

| Code | Peptide No. | Sequence | SEQ ID NO. | Formula | M.W. | Purity in % |
|---|---|---|---|---|---|---|
| Bio-Target-PEP | Biotin-FR-27 | Biotin-FNWYVDGVEVHNAKTKPREEQYNSTYR | 7 | $C_{159}H_{230}N_{44}O_{48}S_1$ | 3557.94 | 98.64 |
| KLH-Target-PEP | KLH-CR-28 | KLH-CYS-FNWYVDGVEVHNAKTKPREEQYNSTYR | 7 | $C_{152}H_{221}N_{43}O_{47}S_1$ | 3434.77 | 96.74 |
| Control-Cyno-Pep | Control peptide #1 (Cyno): Biotin-FR-27 | Biotin-FNWYVNGAEVHHAQTKPRETQYNSTYR | 8 | $C_{157}H_{224}N_{46}O_{46}S_1$ | 3523.8 | 95.75 |
| Control-Rat-Pep | Control peptide #2 (Rat): Biotin-FR-27 | Biotin-FSWFVDDVEVHTAQTRPPEEQFNSTFR | 9 | $C_{158}H_{223}N_{41}O_{48}S_1$ | 3496.77 | 95.45 |

FIGS. 4A, 5A, 6A, and 7A show the HPLC profiles of the peptides Biotin-FR-27, KLH-CR-28, Control peptide #1 and Control peptide #2, respectively. FIGS. 4B, 5B, 6B, and 7B show the MS profiles of the peptides Biotin-FR-27, KLH-CR-28, Control peptide #1 and Control peptide #2, respectively The immunization time line is provided in Table 2 Shown below.

TABLE 2

| Steps | Day | Description |
|---|---|---|
| Pre-bleed Collection | 1 | Pre-immune serum is collected as negative control. |
| Primary Injection | 1 | Group 1: 200 µg KLH-Target-PEP is mixed 1:1 with CFA and inject via tail vein injection for each shark, 5 in total. Group 2: 100 µg Target-PRO and 100 µg KLH-Target-PEP is mixed 1:1:2 with CFA and inject via tail vein injection for each shark, 5 in total. |
| 2$^{nd}$ Injection | 34 | Group 1: 200 µg KLH-Target-PEP is mixed 1:1 with IFA and inject via tail vein injection for each shark, 5 in total. Group 2: 100 µg Target-PRO and 100 µg KLH-Target-PEP is mixed 1:1:2 with IFA and inject via tail vein injection for each shark, 5 in total. |
| 3$^{rd}$ Injection | 64 | Group 1: 200 µg KLH-Target-PEP is mixed 1:1 with IFA and inject via tail vein injection for each shark, 5 in total. Group 2: 100 µg Target-PRO and 100 µg KLH-Target-PEP is mixed 1:1:2 with IFA and inject via tail vein injection for each shark, 5 in total. |
| Bleeding and Titration | 90 | ELISA titration of pre-immune and test-serum. |
| 4$^{th}$ Injection | 100 | Group 1: 200 µg KLH-Target-PEP is mixed 1:1 with IFA and inject via tail vein injection for each shark, 5 in total. Group 2: 100 µg Target-PRO and 100 µg KLH-Target-PEP is mixed 1:1:2 with IFA and inject via tail vein injection for each shark, 5 in total. |
| Bleeding and Titration | 125 | ELISA titration of pre-immune and test-serum. |

Blood samples were taken from each shark after immunization, lymphocytes were isolated from Peripheral blood and total RNA was prepared for each bleeding. After the fourth injection, the test bleed was collected and the 2$^{nd}$ antisera titration was conducted to monitor the immune response. This time the controls were involved during the test. As shown in Tables 3-6, the immune response of representative sharks from group 2 were enhanced for both protein (better) and peptide targets.

TABLE 3

| Coating Targets (200 ng/well) | Test Samples | 1:1,000 | 1:4,000 | 1:16,000 |
|---|---|---|---|---|
| Target - PRO | Pre-ImmuneSera | 0.0590 | 0.0610 | 0.0600 |
| | 2$^{nd}$ Test Sera | 0.5285 | 0.1714 | 0.0595 |
| | | 0.5266 | 0.1749 | 0.0615 |
| Control-Rat-Pro | Pre-ImmuneSera | 0.0611 | 0.0773 | 0.0596 |
| | 2$^{nd}$ Test Sera | 0.1172 | 0.0673 | 0.0689 |
| | | 0.1650 | 0.0657 | 0.0656 |
| Control-Cyno-Pro | Pre-ImmuneSera | 0.1065 | 0.0657 | 2.5425 |
| | 2$^{nd}$ Test Sera | 0.1616 | 0.0695 | 1.4408 |
| | | 0.1074 | 0.0658 | 0.4094 |
| Bio-Target-PEP | Pre-ImmuneSera | 0.0629 | 0.0622 | 0.0645 |
| | 2$^{nd}$ Test Sera | 0.0899 | 0.0758 | 0.0610 |
| | | 0.0606 | 0.0625 | 0.0635 |
| Control-Rat-Pep | Pre-ImmuneSera | 0.0703 | 0.0675 | 0.0682 |
| | 2$^{nd}$ Test Sera | 0.0696 | 0.0639 | 0.0644 |
| | | 0.0793 | 0.0633 | 0.0681 |
| Control-Cyno-Pep | Pre-ImmuneSera | 0.0625 | 0.0601 | 0.0630 |
| | 2$^{nd}$ Test Sera | 0.0642 | 0.0623 | 0.0634 |
| | | 0.0768 | 0.0662 | 0.0684 |

Shark W101619-G2-2: 2$^{nd}$ shark from Group 2 (injected with Target-PRO and KLH-Target-PEP)
Target-Pro: target protein
Bio-Target-PEP: biotinylated target peptide
Control-Rat-Pro: rat control protein
Control-Cyno-Pro: cyno control protein
Control-Rat-Pep: biotinylated rat control peptide
Control-Cyno-Pep: biotinylated cyno control peptide

TABLE 4

| Coating Targets (200 ng/well) | Test Samples | 1:1,000 | 1:4,000 | 1:16,000 |
|---|---|---|---|---|
| Target - Pro | Pre-ImmuneSera | 0.0563 | 0.0554 | 0.0549 |
| | 2$^{nd}$ Test Sera | 0.3324 | 0.1730 | 0.0590 |
| | | 0.3602 | 0.1630 | 0.0598 |
| Control-Rat-Pro | Pre-ImmuneSera | 0.0581 | 0.0645 | 0.0593 |
| | 2$^{nd}$ Test Sera | 0.1007 | 0.0639 | 0.0597 |
| | | 0.1105 | 0.0770 | 0.0641 |
| Control-Cyno-Pro | Pre-ImmuneSera | 0.0639 | 0.0691 | 0.0627 |
| | 2$^{nd}$ Test Sera | 0.0612 | 0.0650 | 0.0613 |
| | | 0.0630 | 0.0640 | 0.0645 |
| Bio-Target-PEP | Pre-ImmuneSera | 0.0563 | 0.0654 | 0.0549 |
| | 2$^{nd}$ Test Sera | 0.1624 | 0.0630 | 0.0612 |
| | | 0.1602 | 0.0616 | 0.0637 |
| Control-Rat-Pep | Pre-ImmuneSera | 0.0606 | 0.0632 | 0.0631 |
| | 2$^{nd}$ Test Sera | 0.0646 | 0.0682 | 0.0687 |
| | | 0.0678 | 0.0662 | 0.0688 |
| Control-Cyno-Pep | Pre-ImmuneSera | 0.0628 | 0.0611 | 0.0565 |
| | 2$^{nd}$ Test Sera | 0.0655 | 0.0647 | 0.0639 |
| | | 0.0683 | 0.0689 | 0.0630 |

Shark W101619-G2-3: 3rd shark from Group 2 (injected with Target-PRO and KLH-Target-PEP)
Target-Pro: target protein
Bio-Target-PEP: biotinylated target peptide
Control-Rat-Pro: rat control protein
Control-Cyno-Pro: cyno control protein
Control-Rat-Pep: biotinylated rat control peptide

TABLE 5

| Coating Targets (200 ng/well) | Test Samples | 1:1,000 | 1:4,000 | 1:16,000 |
|---|---|---|---|---|
| Target - Pro | Pre-ImmuneSera | 0.0606 | 0.0632 | 0.0631 |
| | 2$^{nd}$ Test Sera | 0.5046 | 0.2982 | 0.0987 |
| | | 0.6778 | 0.2162 | 0.1488 |
| Control-Rat-Pro | Pre-ImmuneSera | 0.0609 | 0.0608 | 0.0675 |
| | 2$^{nd}$ Test Sera | 0.2916 | 0.0998 | 0.0614 |
| | | 0.3019 | 0.0960 | 0.0623 |
| Control-Cyno-Pro | Pre-ImmuneSera | 0.0713 | 0.0735 | 0.0623 |
| | 2$^{nd}$ Test Sera | 0.1808 | 0.0680 | 0.0693 |
| | | 0.1918 | 0.0656 | 0.0622 |
| Bio-Target-PEP | Pre-ImmuneSera | 0.0690 | 0.0608 | 0.0640 |
| | 2$^{nd}$ Test Sera | 0.2610 | 0.0618 | 0.0560 |
| | | 0.2790 | 0.0646 | 0.0612 |
| Control-Rat-Pep | Pre-ImmuneSera | 0.0664 | 0.0668 | 0.0664 |
| | 2$^{nd}$ Test Sera | 0.0693 | 0.0692 | 0.0670 |
| | | 0.0628 | 0.0699 | 0.0686 |
| Control-Cyno-Pep | Pre-ImmuneSera | 0.0781 | 0.0650 | 0.0579 |
| | 2$^{nd}$ Test Sera | 0.0695 | 0.0654 | 0.0610 |
| | | 0.0788 | 0.0650 | 0.0566 |

Shark W101619-G2-4: 4$^{th}$ shark from Group 2 (injected with Target-PRO and KLH-Target-PEP)
Target-Pro: target protein
Bio-Target-PEP: biotinylated target peptide
Control-Rat-Pro: rat control protein
Control-Cyno-Pro: cyno control protein
Control-Rat-Pep: biotinylated rat control peptide
Control-Cyno-Pep: biotinylated cyno control peptide

TABLE 6

| Coating Targets (200 ng/well) | Test Samples | 1:1,000 | 1:4,000 | 1:16,000 |
|---|---|---|---|---|
| Target - Pro | Pre-ImmuneSera | 0.0558 | 0.0573 | 0.0523 |
| | 2$^{nd}$ Test Sera | 0.0931 | 0.0742 | 0.0617 |
| | | 0.0923 | 0.0683 | 0.0630 |
| Control-Rat-Pro | Pre-ImmuneSera | 0.0669 | 0.0608 | 0.0684 |
| | 2$^{nd}$ Test Sera | 0.0910 | 0.0618 | 0.0656 |
| | | 0.0979 | 0.0606 | 0.0699 |
| Control-Cyno-Pro | Pre-ImmuneSera | 0.0758 | 0.0657 | 0.0622 |
| | 2$^{nd}$ Test Sera | 0.0825 | 0.0699 | 0.0656 |
| | | 0.0862 | 0.0898 | 0.0635 |
| Bio-Target-PEP | Pre-ImmuneSera | 0.0693 | 0.0619 | 0.0643 |
| | 2$^{nd}$ Test Sera | 0.6970 | 0.0661 | 0.0646 |
| | | 0.0641 | 0.6590 | 0.0513 |
| Control-Rat-Pep | Pre-ImmuneSera | 0.0617 | 0.0689 | 0.0627 |
| | 2$^{nd}$ Test Sera | 0.0655 | 0.0659 | 0.0647 |
| | | 0.0637 | 0.0652 | 0.0611 |
| Control-Cyno-Pep | Pre-ImmuneSera | 0.0640 | 0.0657 | 0.0528 |
| | 2$^{nd}$ Test Sera | 0.0675 | 0.0670 | 0.0563 |
| | | 0.0633 | 0.0606 | 0.0592 |

Shark W101619-G2-5: 5$^{th}$ shark from Group 2 (injected with Target-PRO and KLH-Target-PEP)
Target-Pro: target protein
Bio-Target-PEP: biotinylated target peptide
Control-Rat-Pro: rat control protein
Control-Cyno-Pro: cyno control protein
Control-Rat-Pep: biotinylated rat control peptide
Control-Cyno-Pep: biotinylated cyno control peptide b) PCR Amplification of Specific igNAR Libraries and CDNA Synthesis Primer pairs can be designed using automated software, designed using known design parameters to amplify coding sequences and produce fragments with termini that are appropriate for cloning into an appropriate vector. The primary PCR amplifications can be set up for each library (e.g., CDR3, framework libraries) using the appropriate oligonucleotide primers. Each reaction mixture will typically contain Wobbegong igNARGeneArt cDNA, appropriate forward and reverse primers, dNTPs, Taq DNA polymerase, and 1×PCR reaction buffers. By way of example, reactions will be performed for ~20-30 PCR cycles of 94° C., 20 s; 60° C., 40 s; 72° C., 30 s, followed by 5 minutes at 72° C. Reaction products will be purified. For cDNA synthesis, conventional RT-PCR was used where to each sample, the tRNA nurse sharks was added along with the two primers that are specific for v NAR framework. The primers can also be incorporated with specific restriction sites to allow subsequent cloning into the phagemid vectors.

After cDNA synthesis, the tubes were incubated at 95° C. for 7 min. to inactivate reverse transcriptase and denature the template.

c) Library Preparation

Each of the libraries, the preferred vector DNA, will be digested with appropriate restriction enzymes and purified, for example, using one Wizard PCR clean-up columns. The digested library DNA will be ligated, purified and electroporated into bacterial cells (e.g., *E. coli*). Libraries can also be generated using, for example, the Hi-Affi™ Phage Display Platform, where an immune library with over 108 capacity can be generated to maximize the diversity of shark single-domain heavy chain antibody (shark sdAbs) repertoire. Various libraries can be combined to generate a library of the igNAR variable domain (vNAR) peptide libraries with multiple vNAR variants. The antigen-specific binders (shark sdAbs) can then be screened and isolated through the best-fit biopanning strategy. The selected shark sdAbs specifically recognize the target but do not cross-react with the negative controls. To isolate the monoclonal binders for the target of interest, a group of phage clones are randomly picked and validated by both phage ELISA and soluble ELISA. This two-step validation strategy can contribute to the most reliable data and avoid most of false positive results. The DNA sequence of the positive clones can be obtained during this stage, and be analyzed properly to identified the unique clones. The selected binders can be further characterized, including by, but not limited to sequencing, binding assay, affinity measurement, stability evaluation, epitope/paratope mapping, and functional assays. Further development of the shark sdAbs can be achieved using methods known to a person of skill in the art, such as affinity maturation, specificity optimization, stability improvement, multivalent development (e.g. bispecific sdAb), ADC development, and CAR development. For the production and manufacture of the selected shark sdAbs, we can also generate recombinant shark sdAbs with desired expression systems through either transient transfection or the construction of stable cell line.

d) Expression of vNARs

Experimental design, procedures and protocols will be designed with a goal to produce sufficient amounts of recombinant vNARs for production of protein arrays. An insect cell based system or a baculovirus-based expression systems are typically used for protein production. Select cDNAs (and controls) will be prepared for transformation into the appropriate expression system (e.g., bacmid-containing *E. coli* strain). Following transformation, positive colonies will be picked robotically, DNA isolated and will be transfected into chosen expression system (e.g., insect cells) Following growth, the cells containing expressed proteins will be collected and lysed in preparation for purification. For the production and manufacture of the selected shark sdAbs, recombinant shark sdAbs can be generated with desired expression systems through either transient transfection or the construction of stable cell line.

e) Purification

Protein purification can be optimized and automated through a high-throughput protein purification process so that more than 5000 different proteins can be purified in a single day in a 96-well format. All steps of the process including cell lysis, binding to affinity resins, washing, and elution, will be integrated into a fully automated robotic process which will be carried out at 4° C. Cells expressing desired vNARs (e.g., insect cells) will be lysed under non-denaturing conditions and lysates will be loaded directly into 96-well plates containing an affinity resin (e.g., glutathione or Ni-NTA resin). After washing, purified proteins will be eluted under conditions designed to obtain native proteins. After purification, samples of the purified material will be compared with crude protein samples obtained from aliquots of cells that have been vigorously lysed and denatured. The two sample sets can be run out on SDS-PAGE gels and immuno-detected by Western blot. The protein sizing data for both crude and purified protein fractions will be collected and the presence of a dominant band at the correct expected molecular weight will be ascertained.

Example 2: Method for Making Protein Arrays with Immunoglobulin Molecules Derived from Shark igNARs This Example illustrates a method that can be employed to make protein arrays with immunoglobulin molecules derived from shark igNARs.

Immobilization of vNAR variants on solid surfaces, such as chips, can be achieved by (non-covalent) adsorption or by directed covalent coupling by using amino groups (of lysine or of the amino terminus) of the vNARs to activated carboxyl groups at the solid surface by conventional carbodiimide coupling using 1, ethyl-3-[3-dimethyl aminopropyl] carbodiimide (EDC) and N-hydroxysuccinimide (NHS). Alternatively, special tag-sequences can be used to direct non-covalent binding to an immobilized molecule, which interacts with this tag. As an example, biotin-streptavidin based tags can be used. Immobilization is facilitated by the biotin due to the high affinity interaction with immobilized streptavidin on the substrate.

Alternatively, a microarray comprising vNARs immobilized on a micro glass slide can be printed. Aliquots of each purified vNAR variant will be robotically dispensed in buffer optimized for array printing into microarrayer-compatible bar-coded 384-well plates. The contents of these plates along with plates of proteins that will be used as positive (e.g. fluorescently-labeled proteins, biotinylated proteins, etc.) and negative (e.g. BSA) controls will be spotted onto a substrate (e.g., glass) using a microarrayer robot. A typical lot of microarrays generated from one printing run can include 100 slides. Each of the vNARs can also be tagged with an epitope (e.g. GST or 6×His), and representative slides from each printing lot can be checked for quality/density using a labeled antibody that is directed against specific epitopes.

Example 3: Identification of Novel Proteins

This Example describes a method to identify novel protein from a biological sample.

Experimental Design

To test if human proteins can bind to the protein arrays of the present disclosure, a sample obtained from a human tissue can be prepared by conventional methods known to a person of skill in the art, to be passed over the protein array of the present disclosure. The sample can contain various proteins, including, but not limited to, transcription factors, protein kinases, enzymes, biomarkers and cell cycle regulators. To reveal novel protein interactions, the proteins can be probed against a protein array containing either a single vNAR or more than 1000 different vNAR variants that were expressed, isolated, purified and immobilized on a substrate essentially according to the methods provided in Examples 1-2. After incubation, and washes to remove non-specifically bound proteins, the human proteins that bind specifically to the array (e.g., at least with a nanomolar binding affinity) are eluted. Protein expression levels can be determined using the diagnostic devices of the present disclosure in conjunction with conventional immunoassays know in the field. Examples of such assays are radioimmunoassays, enzyme immunoassays (e.g., ELISA), immunofluorescence immunoprecipitation, latex agglutination, hemagglutination, and histochemical tests, which are conventional methods well-known in the art. By way of example, novel interactions can be revealed using antibodies conjugated to AlexaFluor 647 (anti-V5-AF647) for detection. The novel interactions can be visualized by acquiring images with a fluorescent microarray scanner and displaying with microarray analysis software. Positive controls of human proteins can be used to calibrate the sensitivity of the assay. The assay could be coupled with an ELISA and/or mass spectrometry to identify the novel human proteins bound to the array. From the detection assays described above, identification of the novel protein-protein interactions can also be made.

Example 4: Comparison of Protein Expression in Two Samples

This Example describes a method to compare protein expression pattern in two biological samples and obtain an expression profile.

Experimental Design for Biomarker Quantitation

The purpose of this study is to identify proteins (e.g., biomarkers) expressed in samples obtained from diseased subjects (e.g., ovarian cancer patient) compared to a samples obtained from normal, unaffected subjects or from subjects with an indolent, mild or non-aggressive forms of the disease. Toward this end, sera (or alternatively plasma) will be screened using the protein array comprising vNAR variants. Expression of biomarkers in the samples from diseased subjects and the non-expression of those in the control samples can be ascertained by an ELISA or a mass spectrometry analysis of the proteins specifically bound to the array. Certain currently accepted biomarkers of a diseased state, such as Her-2, a standard marker of in cancer, can be included as positive control to calibrate the assay. Other known proteins can also be included as references to compare the sensitivity and specificity of the protein array. Under the optimized experimental conditions, different concentrations of standard solutions (e.g., HER2) will be analyzed to test the linear range of the assay (for example, a range from 25 pg·mL-1 to 5 ng·mL-1.) The limits of the detection of the assay can also be calculated based on the standards used (for example, a concentration of 9.65 pg·mL-1) and based on the limits of detection, the assays can be applied for clinical testing of diluted samples.

The detection of significant and specific binding from samples from diseased subjects that is not observed in control sera, is indicative of the presence of a biomarker that can be used to correlate to a diseased state or status. If the occurrence of some of the markers in the disease samples proves to be predictive of the disease, then it can be important to determine if there is any correlation with the occurrence of those markers to the prognosis.

Example 5: Use of Protein Arrays as Substrates Suitable for Performing Affinity Capture and Sample Enrichment This Example describes a method to enrich a humanized monoclonal antibody from the plasma of a pre-clinical animal model.

Immunoaffinity LC-MS for the Quantitation of a Monoclonal Antibody Therapeutic

Immobilization of shark igNARs on a substrate to create a protein array as described herein can be produced using the method described in Example 2. The substrate can be a pipette tip and/or a plate. Affinity capture can be performed on the herein described protein arrays. Serum samples, for example a sample comprising a monoclonal antibody, can be loaded onto the protein array having the immobilized shark igNARs such that proteins of interest within the sample (e.g., a monoclonal antibody) bind to the immunoglobulin molecules of the protein array. The serum samples can be diluted prior to loading the samples onto the protein array. For example, the serum samples can be diluted with TBS.

The protein array with the loaded serum samples can be washed with NaCl and HEPES followed by a secondary wash with TBS to enrich the sample. The sample can then be eluted from the protein array with, for example, formic acid, and neutralized with a tris-HLC buffer such that the bound proteins of interest (e.g., a monoclonal antibody) is eluted from the protein array.

The eluted sample can then be separated on a liquid chromatography column, for example, a liquid chromatography column comprising a stationary phase having a diphenyl functional group. The liquid chromatography column can be a reverse phase liquid chromatography column. The liquid chromatography column can be coupled to a detector, for example, a mass spectrometer. The mass spectrometer can be a QTOF mass spectrometer. The purity of the sample can be determined.

This affinity capture method can be used for a variety of samples that include mammalian cells or a population of mammalian cells. The protein of interest can be, for example, human immunoglobulin Fc domains, human IgG light chain kappa domains, human IgG light chain lamba domains, monocyte chemoattractant protein MCP-1/CCL2, vascular endothelial growth factor A (VEGF-A), tumor necrosis factor alpha (TNF-a), interleukin 6 (IL-6), thyroglobulin, insulin, modified insulin drugs, ghrelin, drugs of abuse and their metabolites, hemoglobin, albumins, glucagon, viral vectors and their capsid proteins, adenoassociated virus, lentivirus, gamma retrovirus, adenovirus, hepatitis c, hepatitis b, hepatitis a, HIV, biomarkers for cardiovascular disease, human growth hormone, erythropoietin, cancer immunotherapy biomarkers, host cell proteins from murine and chinese ovary hamster cells, amyloid beta, tau, phospho-tau, muromonab, edrecolomab, capromab, ibritumomab tiuxetan, blinatumomab, abciximab, rituximab, basiliximab, infliximab, cetuximab, brentuximab vedotin, siltuximab, palivizumab, trastuzumab, alemtuzumab, omalizumab, bevacizumab, natalizumab, ranibizumab, eculizumab, certolizumab, tocilizumab, pertuzumab, obinutuzumab, trastuzumab emtansine, pembrolizumab, vedolizumab, elotuzumab, idarucizumab, mepolizumab, adalimumab, pegfilgrastim, panitumumab, romiplostim, canakinumab, golimumab, ofatumumab, ustekinumab, denosumab, belimumab, ipilimumab, raxibacumab, efmoroctocog alfa, eftrenonacog alfa, nivolumab, ramucirumab, alirocumab, asfotase alfa, daratumumab, evolocumab, necitumumab, secukinumab, abatacept, rilonacept, aflibercept, belatacept, or a combination thereof.

Example 6: Construction of Recombinant AAV Vectors for Expression of Shark sdAbs and Enrichment of Capsids with Full Vector Genomes This Example describes a method to construct and enrich AAV vector preparations. The AAV vectors described herein comprise a polynucleotide sequence encoding at least one shark sdAbs with comprising an amino acid sequence set forth in any one of the four sequences, 4HGK (SEQ ID NO.2), 2COQ (SEQ ID NO.3), 1SQ2 (SEQ ID NO.4) and 2125 (SEQ ID NO.5). Methods and protocols for the preparation and purification of AAV vectors may be found in U.S. Pat. No. 7,220,577 (specifically incorporate herein in its entirety by express reference thereto).

An AAV vector designed to express a reporter gene (e.g., GFP gene) and at least one gene encoding at least one shark sdAbs comprising an amino acid sequence set forth in any one of the four sequences, 4HGK (SEQ ID NO.2), 2COQ (SEQ ID NO.3), 1SQ2 (SEQ ID NO.4) and 2125 (SEQ ID NO.5) can be constructed by conventional techniques using commercially available vectors (e.g., pEGFP-C1 (Clontech)), containing the requisite restriction sites. In some instances, a triple transfection of cells (e.g., 293T cells) will be performed with the rep-AAP helper, rAAV mCherry-caplox71/66 genome and the adenoviral helper construct pHelper to ensure generation of recombinant virus with the heterologous gene expression. The AAV vectors comprising the polynucleotides encoding at least one shark sdAbs can be transfected into cells (e.g., human 293 and HeLa cells) to assess the level of expression of the marker (e.g., GFP) protein obtained from each construct. Expression levels from the AAV constructs will be compared to the level obtained after transfection of the control plasmid.

The AAV serotype vector preparations (e.g., AAV1, AAV5) described herein can be enriched by resolving an empty genome-free, partial genome-containing, and full genome-packaging virus particles as well as contaminants such as capsid fragments and genomes. An AAV serotype vector preparations (e.g., AAV1, AAV5) harboring shark sdAbs can produced by either triple transfection or the producer cell line method and purified via AVB Sepharose High Performance chromatography, as described in Wang Et al., *Mol Ther Methods Clin Dev.* 2015; 2: 15040. AUC analysis of the AVB eluate can be performed for serotype vector preparations (e.g., AAV1, AAV5) by either triple transfection or the producer cell line method to reveal that the fractional content of empty particles. The AAV serotype vector preparations (e.g., AAV1, AAV5) following affinity chromatography will have both empty and full particles, irrespective of serotype. A reduction in the fractional content of empty particles in AAV serotype vector preparations (e.g., AAV1, AAV5) can be achieved using Ion exchange chromatography (IEX). AUC analysis of the IEX eluate can be performed for serotype vector preparations (e.g., AAV1, AAV5) by either triple transfection or the producer cell line method to reveal that the fractional content of empty particles can be significantly reduced. Mass Spectroscopy (e.g., charge detection mass spectrometry (CDMS)) can also be used to detect and determine the difference between the measured masses of the empty particles and the heterogeneous genome (e.g., shark sdAb) containing particles.

The two-column purification method (i.e., AVB-IEX chromatography) described herein can be used to enrich a range of AAV serotypes including but not limited to, AAV2, AAVrh8R, AAV6, and AAVDJ. For all serotypes evaluated, the IEX chromatography will result in a significant decrease in the fractional content of empty capsids. Additionally, IEX chromatography can be useful for the removal of empty capsids from affinity-purified AAV serotype vector preparations.

The in vivo performance of the AAV serotype vector preparations following AVB-IEX chromatography can be assessed by injecting the AAV vector into an appropriate animal model (e.g., mice). The expression of a selectable marker (e.g., GFP) incorporated into the AAV vector can be used as an easy read-out for the efficiency of the transduced vectors. The target specificity of the AAV vector can also be assessed by determining the expression of the selectable marker in different tissues at different time points post-injection.

---

What is claimed is:

1. A protein array comprising: a plurality of immunoglobulin molecules derived from shark single-domain heavy chain antibody lacking light-chains and comprising at least one variable antigen-binding domain, wherein each of the plurality of immunoglobulin molecules comprises at least one binding site for an antigen, and wherein the plurality of immunoglobulin molecules are immobilized on a substrate via a linker, wherein the plurality of immunoglobulin molecules comprises the variable antigen-binding domain with an amino acid sequence of SEQ ID NO: 1.

2. The protein array according to claim 1, wherein the plurality of immunoglobulin molecules comprises a single type of immunoglobulin molecule that binds to same epitopes in the antigen.

3. The protein array according to claim 1, wherein the plurality of immunoglobulin molecules comprises at least two types of immunoglobulin molecules that bind to different epitopes in the antigen.

4. The protein array according to claim 1, wherein the plurality of immunoglobulin molecules comprises at least two types of immunoglobulin molecules, each of which is capable of binding two different antigens.

5. The protein array according to claim 1, wherein the plurality immunoglobulin molecules comprises at least two complementarity determining regions (CDRs).

6. The protein array according to claim 5, wherein the plurality of immunoglobulin molecules further comprises at least two hypervariable loops that have a function that is equivalent to the function of a third CDR region.

7. The protein array according to claim 1, wherein one or more amino acid residues in a framework region of the plurality of immunoglobulin molecules is substituted by a different amino acid to facilitate immobilization on the substrate.

8. The protein array according to claim 7, wherein a C-terminal residue of the plurality of immunoglobulin molecules is substituted with a cysteine residue.

9. The protein array according to claim 8, wherein a C-terminal residue of the plurality of immunoglobulin molecules is substituted with a non-natural amino acid residue.

10. The protein array according to claim 1, wherein one or more amino acid residues are appended to a C-terminus of the plurality of immunoglobulin molecules.

11. The protein array according to claim 10, wherein a poly Histidine tag is appended to the plurality of immunoglobulin molecules.

12. The protein array according to claim 10, wherein a peptide with SEQ ID NO. 6 is appended to the plurality of immunoglobulin molecules.

13. The protein array according to claim 10, wherein a cysteine residue is appended to the plurality of immunoglobulin molecules.

14. The protein array according to claim 10, wherein a non-natural amino acid residue is appended to the immunoglobulin molecule.

15. The protein array according to claim 14, wherein the non-natural amino acid residue is selected from a group consisting of p-acetylphenylalanine, p-azidomethyl-L-phenylalanine and N6-((2-azidoethoxy)carbonyl)-L-lysine.

16. The protein array according to claim 1, wherein the plurality of immunoglobulin molecules are immobilized on the substrate by the linker through a covalent linkage.

17. The protein array according to claim 16, wherein the covalent linkage is achieved by one or more processes selected from group consisting of a NHS activated electrophilic substitution, a carbodiimide dehydration and a Michael addition reaction.

18. The protein array according to claim 1, wherein the plurality of immunoglobulin molecules are attached to the substrate by a cleavable linker.

* * * * *